United States Patent [19]

Ross et al.

[11] Patent Number: 5,958,425
[45] Date of Patent: Sep. 28, 1999

[54] VIRAL VACCINES

[75] Inventors: Louis Joseph Norman Ross, Newbury, United Kingdom; Simon David Scott, Amsterdam, Netherlands; Matthew McKinley Binns, Cambs, United Kingdom

[73] Assignee: Rhone Merieux, Lyons, France

[21] Appl. No.: 08/938,336

[22] Filed: Sep. 25, 1997

Related U.S. Application Data

[62] Division of application No. 08/654,931, May 29, 1996, Pat. No. 5,744,143, which is a division of application No. 08/462,591, Jun. 5, 1995, which is a division of application No. 08/081,932, Jun. 23, 1993, Pat. No. 5,558,860, which is a continuation-in-part of application No. 07/669,392, Apr. 29, 1991, abandoned.

[30] Foreign Application Priority Data

Sep. 13, 1988 [GB] United Kingdom .................... 8821441
Sep. 13, 1989 [WO] WIPO ...................... PCT/GB89/01076

[51] Int. Cl.$^6$ ..................................... A61K 39/255
[52] U.S. Cl. .................................. 424/229.1; 435/320.1; 514/44; 536/23.72
[58] Field of Search ...................... 424/229.1; 435/320.1; 514/44; 536/23.72

*Primary Examiner*—James Ketter
*Attorney, Agent, or Firm*—Larson & Taylor

[57] ABSTRACT

A vaccine effective against Marek's disease virus (MDV) comprises (a) an MDV attenuated by virtue of being TK– or (b) a host expressing an MDV antigen, namely the respective MDV homologues of the HSV gB, gC, gD or gH glycoproteins (or antigenic parts thereof) or the respective MDV homologues of the HSV-1 immediate early genes IE-68 or IE-175. The host may be a herpes virus of turkeys (HVT), more particularly HVT in which the MDV antigen is inserted in the HVT homologue of the HSV gC gene, the ribonucleotide reductase (large subunit) gene or the thymidine kinase (TK) gene.

12 Claims, 66 Drawing Sheets

```
TCGAGCTCGCCCGGGGATGTGTTTAGTCACGATAGACATCGGT
         10        20        30        40

TCGCCCAGCCGTCGAATACAGCATTATATTTTAGTGTTG
         50        60        70        80

AAAATGTAGGGCTGCTTCCTCACTTAAAGGAGGAAATGGCT
         90       100       110       120

CGATTCATGTTTCATAGCAGTAGAAAAACAGATTGGACCG
        130       140       150       160

TCAGTAAGTTTAGAGGGTTTTATGACTTTAGCACTATAGA
        170       180       190       200

TAATGTAACTGCGGCCCATCGCCATGGCTTGGAAATATATC
        210       220       230       240

AAAGAACTGATTTTTGCAACAGCTTTATTTCTTCTGTAT
        250       260       270       280

TTAAATGTGGCGAATTGCACATCTGTCGTGCCGACAGTTT
        290       300       310       320

GCAGATCAACAGCAATGGAGACTATGTATGGAAAATGA
        330       340       350       360
```

FIG. 2A

ATATATATAACATATGAAACCGAATATCCACTTATAATGA
          370           380           390           400

TTCTGGGGTCAGAATCAAGCACTTCAGAAACGCAAAATAT
          410           420           430           440

GACTGCAATTATTGATACAGATGTTTTTTCGTTGCTTTAT
          450           460           470           480

TCTATTTTGCAGTATATGGCCCCCGTTACGGCAGATCAGG
          490           500           510           520

TGCGAGTAGAACAGATTACCAACAGCCACGCCCCCATCTG
          530           540           550           560

ACCCGTCCAATATTCTTGTGTCCCTGCATTTTATCTCACA
          570           580           590           600
                                                 M  H
CAATTTATGAACAGCATTAAGATCATCTCACTATGCA
          610           620           630           640
 Y  F  R  R  N  C  I  F  F  L  I  V  I
CTATTTTAGGCGGAATTGCATTTTTTTCCTTATAGTTATT
          650           660           670           680

*FIG. 2B*

```
L  Y  G  T  N  S  S  P  S  T  Q  N  V  T
CTATATGGTACGAACTCATCTCCGAGTACCCAAAATGTGA
          690            700           710          720

S  R  E  V  V  S  S  V  Q  L  S  E  E
CATCAAGAGAAGTTGTTTCGAGCGTCCAGTTGTCTGAGGA
         730           740           750          760

E  S  T  F  Y  L  C  P  P  P  V  G  S
AGAGTCTACGTTTTATCTTTGTCCCCACCAGTGGGTTCA
         770           780           790          800

T  V  I  R  L  E  P  P  R  K  C  P  E  P
ACCGTGATCCGTCTAGAACCGCCGAAAATGTCCCGAAC
         810           820           830          840

R  K  A  T  E  W  G  E  G  I  A  I  L
CTAGAAAAGCCACCGAGTGGGGTGAAGGAATCGCGATATTA
         850           860           870          880
```

*FIG. 2C*

```
         |--
          F   K   E   N   I   S   P   Y   K   F   K   V   T
        TTTAAAGAGAATATCAGTCCATATAAATTTAAAGTGACGC
        |||||||||||||||||||||||||||||||||||||||
        GAGAATATCAGTCCGTATAAATTCAAAGTAACAC
                890       900       910       920

|--                        --V--
          L   Y   Y   K   N   I   Q   T   T   W   T   G
        TTTATTATAAAAATATCATTCAGACGACGACATGGACGG
        |||||||||||||||||||||||||||||||||||||||
        TTTACTATAAGAACGTTATACAAACTAACGACGTGGACTG
                930       940       950       960

|--
          T   T   Y   R   Q   I   T   N   R   Y   T   D   R
        GGACGACATATAGACAGAGATCACTAATCGATATACAGATAG
        ||||||||||||||||||||||||||||||||||||||||
        GGACGACGTACAGACAGATAACTAACAGGTATACAGATAG
              970       980       990       1000
```

FIG. 2D

```
           -------D------
  T  P  V  S  I  E  E  I  T  D  L  I  D
GACGCCCGTTTCCATTGAAGAGATCACGGATCTAATCGAC
||| ||| ||| ||| ||| ||| ||| ||| ||| |||
AACACCCGTGTCTATCGACGAAATTACTGATTTGATAGAT
     1010       1020       1030       1040

------
           ------K------                     R  N
  G  K  G  R  C  S  S  K  A  R  Y  L  R  N
GGCAAAGGAAGATGCTCATCTAAAGCAAGATACCTTAGAA
||| ||| ||| ||| ||| ||| ||| ||| ||| |||
GGTAAGGGGAAATGTTCATCCAAAGCCCGGTATCTTTCG
     1050       1060       1070       1080

N  V  Y  V  E  A  F  D  R  D  A  G  E
ACAATGTATATGTTGAAGCGTTTGACAGGATGCGGGAGAA
     1090       1100       1110       1120

K  Q  V  L  L  K  P  S  K  F  N  T  P
AAACAAGTACTTCTAAAACCATCAAAATTCAACACGCCCC
     1130       1140       1150       1160
```

FIG. 2E

```
      E  S  R  A  W  H  T  N  E  T  Y  T  V
   GAATCTAGGGCATGGCACACGACTAATGAGACGTATACCG
                     |||||||||||||||||||||
                     GGCATGGCATACGACCAACGAGACGTACACCG
   1170       1180       1190       1200

V
      W  G  S  P  W  I  Y  R  T  G  T  S  V
   TGTGGGGATCACCATGGATATATCGAACGGGAACCTCCGT
   |||||||||||||| ||||||||||||||||||||||||
   TGTGGGGATCTCCATGGTATATAGAACGGGCACGTCCGT
   1210       1220       1230       1240

A
      N  C  I  V  E  E  M  D  A  R  S  V  F
   CAATTGTATAGTAGAGGAAATGGATGCCCGCTCTGTGTTT
   ||| ||| ||||||||| |||||||||||||||||||||
   CAACTGCATAGTAGAGAAGAGATGGATGCCAGATCAGCATTT
   1250       1260       1270       1280
```

FIG. 2F

```
                ----T--:-----:-----:-----:-----:-----:----- N
                    P  Y  S  Y  F  A  M  A  N  G  D  I  A  N
                 CCGTATTCATATTTTGCAATGGCCAATGGCGACATCGCGA
                  ||   |   | |||||||||||||||||||| ||||||||
                 CCATACACGTACTTTGCAATGGCCAATGGAGATATCGCAA
                    :    :    :    :
                   1290 1300 1310 1320

----M-:-----:T----:T--:-D-----:-----:----- A
                    I  S  P  F  Y  G  L  S  P  P  E  A  A
                 ACATATCTCCATTTTATGGTCTATCCCCACCAGAGGCTGC
                 ||||| |||||||||| ||       |||| |||| |
                 ACATGTCTCCATTTTATGAACAACTCCAACCGACGCGGC
                    :    :    :    :
                   1330 1340 1350 1360

----:----S:-----:-----:R----:-----R-----:- Q
                    A  E  P  M  G  Y  P  Q  D  N  F  K  Q
                 CGCAGAACCCATGGGATATCCCCAGGATAATTTCAAACAA
                 || ||||||||| ||||| |||||||| ||||||||| ||
                 CGCGGAGCCCATGAGCTATCCGCAAGACCGATTCAGGCAA
                    :    :    :    :
                   1370 1380 1390 1400
```

FIG. 2G

```
     -F-------------P---------------T-----
      L   D   S   Y   F   S   M   D   L   D   K   R   R   K
     CTAGATAGCTATTTTTCAATGGATTTGGACAAGCGTCGAA
     ||  ||||||||||||||||||||  ||||||||||  ||||
     TTTGACAGCTATTTCCCATGGATTTGGATACGCCCGAA
              1410        1420        1430        1440

-|
        A   S   L   P   V   K   R   N   F   L   I   T   S
       AAGCAAGCCCTTCCAGTCAAGCGTAACTTTCTCATCACATC
       ||
       AA
              1450        1460        1470        1480

H   F   T   V   G   W   D   W   A   P   K   T   T
       ACACTTCACAGTTGGGTGGGACTGGGCTCCAAAAACTACT
              1490        1500        1510        1520

R   V   C   S   M   T   K   W   K   E   V   T   E   M
       CGTGTATGTTCAATGACTAAGTGGAAAGAGGTGACTGAAA
              1530        1540        1550        1560

L   R   A   T   V   N   G   R   Y   R   F   M   A
       TGTTGCGTGCAACAGTTAATGGGAGATACAGATTTATGGC
              1570        1580        1590        1600
```

FIG. 2H

```
R   E   L   S   A   T   F   I   S   N   T   T   E
CCGTGAACTTTCGGCAACGTTTATCAGTAATACGACTGAG
      1610        1620        1630        1640

F   D   P   N   R   I   I   L   G   Q   C   I   K   R
TTTGATCCAAATCGCATCATATTAGGACAATGTATTAAAC
      1650        1660        1670        1680

E   A   E   A   A   I   E   Q   I   F   R   T   K
GCGAGGCAGAAGCAGCAATCGAGCAGATATTTAGGACAAA
      1690        1700        1710        1720

Y   N   D   S   H   V   K   V   G   H   V   Q   Y
ATATAATGACAGTCACGTCAAGGTTGGACATGTACAATA
      1730        1740        1750        1760

F   L   A   L   G   G   F   I   V   A   Y   Q   P   V
TTTCTTGGCTCTCGGGGATTTATTGTAGCATATCAGCCTG
      1770        1780        1790        1800

L   S   K   S   L   A   H   M   Y   L   R   E   L
TTCTATCCAAATCCCTGGCTCATATGTACCTCAGAGAATT
      1810        1820        1830        1840
```

*FIG. 21*

```
M   R   D   N   R   T   D   E   M   L   D   L   V
GATGAGAGACAACAGGACCGATGAGATGCTCGACCTGGTA
        1850            1860            1870            1880

N   N   K   H   A   I   Y   K   K   N   A   T   S   L
AACAATAAGCATGCAATTTATAAGAAAAATGCTACCTCAT
        1890            1900            1910            1920

S   R   L   R   R   D   I   R   N   A   P   N   R
TGTCACGATTGCGGCGAGATATTCGAAATGCACCAAATAG
        1930            1940            1950            1960

K   I   T   L   D   D   T   T   A   I   K   S   T
AAAAATAACATTAGACGACACCACAGCTATTAAATCGACA
        1970            1980            1990            2000

S   S   V   Q   F   A   M   L   Q   F   L   Y   D   H
TCGTCTGTTCAATTCGCCATGCTCCAATTTCTTTATGATC
        2010            2020            2030            2040

I   Q   T   H   I   N   D   M   F   S   R   I   A
ATATACAAACCCATATTAATGATATGTTTAGTAGGATTGC
        2050            2060            2070            2080
```

FIG. 2J

```
         T  A  W  C  E  L  Q  N  R  E  L  V  L
        CACAGCTTGGTGTGCGAATTGCAGAATAGAGAACTTGTTTTA
              2090      2100      2110      2120

W  H  E  G  I  K  I  N  P  S  A  T  A  S
        TGGCACGAAGGGATAAAGATTAATCCTAGCGCTACAGCGA
              2130      2140      2150      2160

|-------------
                             A  T  L  G  R  R  V  A  A  K  M  L  G
                            GTGCAACATTAGGAAGGAGAGTGGCTGCAAAGATGTTGGG
                                                    ||  || |||||||
                                                    GCCAAAATGTTGGG
                              2170      2180      2190      2200

-----D--------------------------------I--E--T-----S-
     D  V  A  A  V  S  S  C  T  A  I  D  A
    GGATGTCGCTGCTGTATCGAGCTGCACTGCTATAGATGCG
    ||  |||||||  || ||||||  || |||  |||  ||  |
    TGACGATGCCGCCGTATCATCATGTATTGAGACTGATTCA
       2210      2220      2230      2240
```

FIG. 2K

```
-D-------------------------V-----
 E   S   V   T   L   Q   N   S   M   R   V   I   T   S
GAATCCGTCACTTTGCAAAATTCTATGCGAGTTATCACAT
||| || ||||| ||||||||| || ||||| |||| |||
GATTCTGTTACCTTACAAAATTCCATGCGGGTTGTCACCT
         2250          2260          2270          2280

T   N   T   C   Y   S   R   P   L   V   L   F   S
CCACTAATACATGTTATAGCCGACCATTGGTTCTATTTTC
|| |||||||| ||||||||||| ||||||| || ||  |
CTACCAATACTTGTTATAGCCGCCCTTTAGTGTTATTCTC
         2290          2300          2310          2320

-------D---R------D---K------------
 Y   G   E   N   Q   G   N   I   Q   G   Q   L   G
ATATGGAGAAACCAAGGAAACATACAGGACAACTCGGTG
||| ||||||| ||||| ||||||||| |||||| |||||
CTACGGGGACCGACAAGACAAAAATACAAGGACAGTTGGGGG
         2330          2340          2350          2360
```

FIG. 2L

```
                                                                    I-----
----I-----------------------------------------------I-----        E  N  N  E  L  L  P  T  L  E  A  V  E  P
                                                                  AAAACAACGAGTTGCTTCCAACGCTAGAGGCTGTAGAGC
                                                                  ||||||||||||||| ||   || |||| ||||||||||
                                                                  AAAACAATGAATTGATTCCAACTCTAGAGGCCATAGAGC
                                                                     2370        2380        2390      2400

C  S  A  N  H  R  R  Y  F  L  F  G  S
      CATGCTCGGCTAATCATCGTAGATATTTTCTGTTTGGATC
      |||  |||||||||| ||||||||||||||||||||||||
      CATGTTCGGCCAATCATCATCGTAGA
         2410        2420         2430        2440

G  Y  A  L  F  E  N  Y  N  F  V  K  M
      CGGTTATGCTTTATTTGAAAACTATAATTTTGTTAAGATGG
             2450        2460        2470        2480

V  D  A  A  D  I  Q  I  A  S  T  F  V  E
      TAGACGCTGCCGATATACAGATTGCTAGCACATTTGTCG
             2490        2500        2510        2520
```

FIG. 2M

```
      L   N   L   T   L   L   E   D   R   E   I   L   P
  AGCTTAAATCTAACCCTGCTAGAAGATCGGGAAATTTGCC
            2530          2540          2550          2560

L   S   V   Y   T   K   E   E   L   R   D   V   G
  TTTATCCGTTTACACAAAGAAGAGTTGCGTGATGTTGGT
            2570          2580          2590          2600

V   L   D   Y   A   E   V   A   R   R   N   Q   L   H
  GTATTGGATTATGCAGAAGTAGCTCGCCGCAATCAACTAC
            2610          2620          2630          2640

E   L   K   F   Y   D   I   N   K   V   I   E   V
  ATGAACTTAAATTTTATGACATAAACAAAGTAATAGAAGT
            2650          2660          2670          2680

D   T   N   Y   A   F   M   N   G   L   A   E   L
  GGATACAAATTACGCGTTTATGAACGGTTTGGCCGAATTG
            2690          2700          2710          2720

F   N   G   M   G   Q   V   G   Q   A   I   G   K   V
  TTTAACGGTATGGGTCAGGTAGGGCAAGCTATAGGCAAAG
            2730          2740          2750          2760
```

FIG. 2N

```
      V  V  G  A  A  G  A  A  I  V  S  T  I  S
      TTGTAGTAGGGGCTGCCGGTGCAATCGTATCTACCATATC
         2770        2780        2790        2800

G  V  S  A  F  M  S  I  P  L  G  L  S
      TGGTGTCTCTGCTTTCATGTCAATCCCTTTGGGGCTTTCG
         2810        2820        2830        2840

A  I  G  L  I  I  A  G  L  V  A  A  F
      GCAATCGGTTTAATCATTATAGCAGGACTCGTGGCTGCAT
         2850        2860        2870        2880

L  A  Y  R  Y  V  N  K  L  K  S  N  P
      TTTTAGCATATCGTTATGTAAACAAGCTTAAAAGCAATCC
         2890        2900        2910        2920

M  K  A  L  Y  P  M  T  T  E  V  L  K
      AATGAAAGCCCTTTATCCTATGACAACAGAAGTGCTTAAG
         2930        2940        2950        2960

A  Q  A  T  R  E  L  H  G  E  E  S  D  D
      GCACAGGCAACGCGTGAGTTGCATGGCGAGGAATCAGATG
         2970        2980        2990        3000
```

FIG. 20

```
         L   E   R   T   S   I   D   E   R   K   L   E   E
      ATTTGGAACGAACACATCTATTGATGAAAGAAAATTAGAAGA
               3010           3020           3030           3040

A   R   E   M   I   K   Y   M   A   L   V   S   A
      AGCTAGAGAAATGATAAAATATATGGCGTTAGTCTCCGCG
               3050           3060           3070           3080

E   R   H   E   K   K   L   R   K   R   R   G
      GAAGAACGCCACGAGAAAAACTGCGGAGAAAGAGGCGAG
               3090           3100           3110           3120

T   T   A   V   L   S   D   H   L   A   K   M   R
      GCACTACCGCCGTTCTATCGGACCACCTGGCAAAAATGAG
               3130           3140           3150           3160

I   K   N   S   N   P   K   Y   D   K   L   P   T
      GATTAAAAATAGTAACCCTAAATATGATAAGTTACCTACT
               3170           3180           3190           3200

T   Y   S   D   S   E   D   D   A   V   *
      ACATATTCAGACTCAGAAGATGATGCTGTGTAAGTGGGCA
               3210           3220           3230           3240

CTATTATATTTGAACTGAATAAAACGCATAGAGCATGATA
               3250           3260           3270           3280
```

FIG. 2P

TGGTTTACTCATTATTGCCGAGATATAAAGCATATTCAAT
3290      3300      3310      3320

ACGATATATTGCCGAACGTGATGCTAAAAACATAGCTCCCT
3330      3340      3350      3360

GTATTATTGATGCGCCATCATTTGATTAATAAATACATCG
3370      3380      3390      3400

ACGCCGGCATCACTGGTGCGGTGTATACCAGCTACGGCGC
3410      3420      3430      3440

TAGCATTCATGGTATCCCGTGATTGCTCGATGCTTTCCTT
3450      3460      3470      3480

CTGAATTCCGTCGGAACGCTCCTGAGAGATGGTCGCAGTT
3490      3500      3510      3520

ATTGGTACATTTCGACCAGCCTCCGGATCTGAAACTGGCA
3530      3540      3550      3560

CAGGAATGCACCGTGGAATTGGTAGAAGTTTTTCCTTCCG
3570      3580      3590      3600

TGGAAGGCATAGGGCGTTCGACTCCCATGGGCCATGAAACTGTGTGGGATGT
         3610          3620          3630          3640          3650

```
TATTATTGGTCCATGCTAGAATAGTCATACGCTACGATCT
         10        20        30        40
GTTGCTATATATGACTATCGCCAAACTGTTAAACCCGCGA
         50        60        70        80
AGAATATATTTCATATATAAACCTAAGGGCCCCTCAGTCTGA
         90       100       110       120
                        M   K   F   Y   C   L
TTTTTTGTGAAAACGTGTATACCATGAAGTTTTACTGCCT
         130       140       150       160
 I   R   F   M   I   A   N   L   Y   S   S   Y
AATCCGTTTCATGATCATAGCGAATCTTTATTCATCTTAC
         170       180       190       200
 Q   I   S   L   P   G   T   Y   P   S   Q   I   L   L
CAAATATCGCTTCCAGGCACATATCCATCCATCGCAAATATTGC
         210       220       230       240
 D   M   K   N   S   P   L   V   R   F   N   I   S
TTGACATGAAGAACTCGCCCGCTCGTACGCTTTAATATATC
         250       260       270       280
```

FIG. 4A

```
 T  R  D  Y  K  D  E  T  L  W  I  R  K
GACGCGTGATTATAAAGACGAGACACTCTGGATACGGAAA
            290        300        310        320

N  S  T  F  V  Y  I  D  T  A  V  T  T  A
AATTCGACATTTGTTTATATCGATACGGCTGTGACGACAG
       330        340        350        360

N  V  I  F  Y  L  P  I  G  Q  V  R  Q
CGAACGTTATCTTTTTATCTGCCGATCGGTCAGGTACGACA
       370        380        390        400

M  V  F  F  K  R  P  I  S  R  L  L  T
AATGGTTTTTTTCAAGCGTCCAATATCCAGGCTACTAACG
       410        420        430        440

S  N  N  L  V  K  F  I  N  T  G  S  Y  A
TCCAATAACCTGGTTAAATTTATTAATACCGGTTCATACG
       450        460        470        480

N  H  T  F  K  T  E  L  S  P  Y  L  S
CCAATCATACATTCAAGACAGAACTTCACCCTATTTGTC
       490        500        510        520
```

FIG. 4B

```
         K   T   N   T   P   L   K   K   Y   E   I   V   V
        GAAAACCAATATACACCGTTGAAGAAATATGAAATTGTTGTC
                    530          540          550         560

D  Q   P   T   G   E   N   P   P   A   G   F   G   S
        GATCAACCTACTGGAGAGAAACCCTCCGGCAGGGGTTCGGAA
                 570          580          590         600

L   K   P   A   D   F   L   N   P   G   Y   K   F
        GTTTAAAACCGGCAGACTTTCTCAACCCCGGATACAAGTT
                    610          620          630         640

V   L   T   S   E   L   V   G   A   Y   T   K   R
        CGTTCTCACAAGCGAGTTGGTAGGAGCCTACACAAAACGA
                    650          660          670         680

S   C   F   V   D   P   M   D   S   L   V   P   I   D
        TCTTGTTTTGTCGATCCGATGGATTCTCTCGTCCCGATAG
                 690          700          710         720

Y   D   H   V   R   T   I   I   F   G   S   A   G
        ATTATGATCATGTACGAACCATTATATTCGGATCTGCTGG
                    730          740          750         760
```

*FIG. 4C*

```
       M  E  I  L  M  K  M  G  I  T  L  L  A  S
       GATGGAGAGATTTAATGAAGATGGGAATTACTTTGGCATCT
               770          780         790         800

M  T  I  S  T  K  Y  N  P  P  I  E  L  I
ATGACCATTTCGACGAAATATAATCCTCCTATTGAACTGA
        810         820         830         840

I  S  A  K  Y  R  N  L  S  L  L  W  P
TAATATCTGCAAAGTACCGAAATTTATCACTGTTGTGGCC
        850         860         870         880

P  R  Q  Q  Y  E  P  V  N  K  G  T  G
ACCCCGACAACAATATGAACCTGTAAATAAAGGGACTGGA
        890         900         910         920

R  P  H  W  I  Y  L  L  G  V  Y  R  N  V
CGCCCCCATTGGATCTACCTATTAGGTGTGTATAGAAACG
        930         940         950         960

S  D  S  E  R  D  S  Y  M  N  M  I  K
TTTCGGACTCCGAGCGTGACTCATACATGAATATGATTAA
        970         980         990        1000
```

FIG. 4D

```
  S   L   G   D   S   M   D   Y   H   F   L   I   S
GAGTCTGGGGCGGATTCTATGGATTATCACTTCCTAATTAGC
         1010           1020           1030           1040

R   A   H   A   Q   M   L   I   L   A   A   E   D   R
AGAGGCGCATGCCCAGATGCTGATACTGGCAGCAGAGGACC
    1050           1060           1070           1080

L   V   D   E   M   H   S   F   R   N   V   I   A
GGCTCGTGGATGAAATGCATAGTTTCAGGAACGTTATTGC
    1090           1100           1110           1120

R   L   F   V   S   L   F   A   F   I   R   N   A
GCGTTTATTTGTATCGTTGTTCGCATTCATACGTAACGCA
    1130           1140           1150           1160

F   Q   S   G   Y   T   S   L   N   D   I   E   I
TTTCAGTCTGGCTACACCTCTCTTAATGACATAATTGAAA
    1170           1180           1190           1200

E   A   D   L   R   L   I   V   E   G   I   S   S
TCGAAGCCGATTTGAGGTTAATTGTAGAAGGCATTTCTTC
    1210           1220           1230           1240
```

*FIG. 4E*

```
  A   A   F   R   K   D   A   S   T   H   F   L   I
TGCTGCATTTCGTAAAGACGCTAGTACACACTTTCTTATA
        1250          1260         1270          1280

S   G   T   P   I   K   D   S   K   A   D   L   I   K
TCGGGAACGCCCCATAAAAGATAGCAAAGCGGATTTAATTA
        1290         1300          1310          1320

S   L   L   S   K   V   I   R   P   I   S   G   H
AATCGTTGTGTCTAAAGTCATTCGACCAATTTCCGGACA
         1330          1340         1350          1360

T   R   P   L   S   A   I   Q   H   L   F   L   L
TACACGTCCCTTATCTGCGATACAACATCTATTCCTTTTG
        1370          1380          1390         1400

R   S   A   Y   A   L   D   I   P   R   Q   N   G   S
AGATCCGCTTATGCATTGGATATACCCCGTCAAAACGGAT
        1410         1420         1430           1440

L   S   E   Q   V   S   T   V   A   L   S   F   I
CTTTGAGCGAACAGGTATCTACAGTGGCACTGTCGTTCAT
        1450         1460          1470          1480
```

*FIG. 4F*

```
           E  N  I  H  S  E  A  M  R  D  I  L  S
         TGAAAATATTCACAGGCGAGGCCATGAGGGACATTCTGTCA
             1490      1500      1510      1520

W  N  T  T  K  H  A  L  Y  Y  A  F  A
         TGGAACACTACAACAAAGCATGCGTTGTATTATGCATTCG
             1530      1540      1550      1560

S  I  L  Q  R  P  L  T  E  W  G  A  S
         CGAGTATTTTGCAACGGCCACTGACCGAATGGGGCGCCTC
             1570      1580      1590      1600

R  N  A  R  R  A  I  L  L  A  S  S  M
         AAGAAATGCACGGAGGCAATACTATTAGCATCATCGATG
             1610      1620      1630      1640

C  T  E  E  H  V  I  A  T  E  L  A  I  Q
         TGTACAGAAGAGCATGTTATCGCAACTGAGTTGGCTATTC
             1650      1660      1670      1680

E  L  Y  V  K  I  R  S  N  A  D  P  I
         AAGAACTGTATGTCAAATCAGAAGTAATGCCGACCCAAT
             1690      1700      1710      1720
```

FIG. 4G

```
H   L   L   D   V   Y   T   P   C   L   S   S   L
ACACCTTCTAGACGTATATACCATGTCTTTCTTCACTA
         1730            1740           1750          1760

R   L   D   L   S   E   H   H   R   I   Y   A   M   A
CGATTGGACCTTTCCGAACACCATCGGATATACGCAATGG
       1770           1780           1790           1800

D   V   V   F   Y   P   D   I   Q   Q   Y   L   K
CAGATGTAGTTTTCTATCCAGACATTCAGCAGTATTTGAA
       1810           1820           1830           1840

K   K   S   H   E   G   N   M   K   E   D   D   L
AAAAAATCCCATGAGGGTAATATGAAGGAAGATGATCTC
       1850           1860           1870           1880

E   T   K   A   E   Y   I   L   T   K   L
GAAACAAAGGCGGAATACATCCTCACCAAGCTT
      1890            1900           1910
```

FIG. 4H

```
AAGCTTTTTGTAAAAAACGATTATGACCACGGACACCCGCT
         10        20        30        40

TTTAGCAATCCTGCCATAAGGTGGTTTCCCGTGCTTGC
         50        60        70        80

CTCGAAGACAATTGCCAGCTAATCCAGCATTACCATATTT
         90       100       110       120

S---Q  -A--L--P
                              M  A  L  P
CCTTGGCTTGCATTTGGATCTGCGCGTCGATGGCATTGCC
                              ATGGCATCTCA
        130       140       150       160

--M---T---S---A---Q-----I
  R   R   P   P   T   L   T   R   V   Y   L   D   G
GAGAAGACCGCCCACGTTAACGCGGAGTTTATCTAGACGGA
|||||||||||||||||||||||||||||||||||||||||
GATGACATCTGCACAGCTCATACGTGTATACCTCGATGGA
        170       180       190       200
```

FIG. 5A

```
-S---M------------------M-------E---I---
 P  F  G  I  G  K  T  S  I  L  N  A  M  P
CCGTTGGTATAGGCAAAACGTCTATACTAAACGCTATGC
   ||||||||||||||  ||||  |||  |||  ||
TCAATGGGTATAGGTAAAACGTCAATGTTGAATGAGATAC       240
        210          220         230

---T-----L|
 D  H  T  P  D  G  A  P  I  L  K  V  Y
CCGACCACGCCCGATGGGGCTCCTATATTGAAAGTGTA         280
||   |
CGACATCTT
  250            260          270

E  P  M  K  Y  W  R  C  Q  S  T  D  L
CGAACCAATGAAATATTGGAGATGCCAGTCTACCGATTTG       320
        290         300         310
```

FIG. 5B

```
              -------R---                                  ---V---T---A
   V  V  A  A  N  E  T  P  E  R  R  R  G  G      ---S---   D  M  I  M  A  S
GTGGTAGCTGCCAACGAAACGCCAGACGTAGGCGTGGTG      GAGCTTTATCACGGATTCCAATCTGACATGATCATGGCATC
   |||||||||||||||||||||||||||||||||||         ||||||||||||||||||||||||||||||||||||||||
             ATCGTCGTCGCAGGG                 GAGAGTTTTCTTTATTTCAATCTAGCATGATTGTAACAGC
          350          360                      370          380          390          400
   330          340

---E---F---L---                              ---V---
   A  L  S  G  F  Q  S  D  M  I  M  A  S        ---L---S---K---              ---V---
                                                I  Q  A  R  F  A  D  P  Y  L  L  F  H
                                             TATACAAGCCAGATTTGCCGATCCATATTTGCTTTTTCAC
                                               ||||||||||||||||||||||||||||||||||||||
                                             TTTACAATCAAAGTTTGCAGATCCCTATCTTGTATTTCAT
                                                410          420          430          440
```

```
            H--R--I--T--G--T--R
     E  R  L  S  K  C  R  G  K  I  E  I  C
GAACGGTTATCATCTAAATGTAGAGGAAAAATAGAAATAT
     |  |  |  |     |  |  |  |  |  |  |
GAGCGGCTTATCGTCGAAGTGTCATCGCATAACAGGAACAC
              450           460           470           480

---G--N-----S--L-----------I---------------I--L--M--L--D--R--H--P---
     D  T  P  A  I  I  L  M  L  D  R  H  P
GCGATACTCCAGCAATTATATATTAATGCTGGATAGGCACCC
     |  |  |  |  |  |     |  |  |     |
GTGGCAATCCATCGCTTATATTAATTCTAGATCGACATCC
              490           500           510           520

---I--S-----T--V----------------------A-----H---------
     V  A  A  I  L  C  F  P  I  T  R  Y  L
TGTGGCGGGGATATTATGTTTCCCAATCACTCGCTATTTA
     |  |  |  |  |        |  |  |  |  |
CATATCCGCTACCGTATGTTTTCCCATTGCTCGACATTTA
              530           540           550           560
```

```
-T----D--C-----------M------              ----Q---P---------V--I---
 L  G  E  Y  S  L  E  M  L  I  S  I  I     R  L  P  L  E  S  P  G  C  N  L  T  V
CTTGGAGAATATTCTTTGGAAATGTTGATTAGCTCTATAA   TAAGACTTCCGTTGGAATCCCCCGGATGCAACCTGACAGT
|||||||||  ||  ||  ||||  ||| ||||  ||||   ||||  ||  ||  ||  |||||||||||  ||| |||
ACTGGAGATTGTTGTTCCTTGGAGAGATGCTAATTAGTATGATAA  TAAGGTTGCCCCAGGAACCGCCAGGATGCAACTTGGTGAT
       570       580       590       600           610       620       630       640

--V--D------H--------S-----L--
 T  I  L  P  D  E  K  E  H  V  N  R  I
CACAATCCTTCCCGACGAAAAGGAACACGTTAATAGGATT
|| |||||| ||| || ||||||||| ||||||  | ||
TGTCGATCTACATGACGAAAAGGAGCATGTTAGCCGTCTA
       650       660       670       680
```

FIG. 5E

```
        S-------N-----T------T------L--L---
        C  S  R  D  R  P  G  E  T  A  D  R  N  M
        TGTTCAAGAGATAGACCGGGTGAAACGGCAGATAGAAATA
         ||||||   |||||  ||||| ||||||  ||||||||
        TCTTCACGGAATAGGACCGGGCGAGAAAACAGATCTACTAA
              690       700       710       720

----S--C--------
                     A            S          L  V  D
            L  R  T  L  N  A  V  Y  A  S  L  V  D
           TGCTCAGAACACTCAATGCCGTATACGCATCTTTGGTGGA
            |||||||  ||||  ||||||||||  |||||||| ||
           TGCTCAGGGCACTTAAATGCAGTGTATTCCTGTTTAGTAGA
                   730       740       750       760

I--M-------H--I-------S----
              T  V  K  Y  A  N  L  T  C  P  Y  E  K
              CACGGTTAAATACGCAAATCTAACATGCCCTTACGAGAAA
               |  ||||||  |||||||||  || |||||| |||||
              CACTATTATGTACGCAAATCATATTTGTCCCTACAGTAAG
                     770       780       790       800
```

FIG. 5F

```
-D--E-------S---------D-------D
 E   W   E   M   E   W   L   G   L   P   W   F   E
GAAAGCTGGGAAATGGAAATGGTTGGGACTTCCCTGGTTTG
         |||   |||||||   ||||||||   ||||   |   ||||
GATGAATGGGAATCTGAATGGTTGGATCTACCATGGTTTG
 E   S   W   E   M   E   W   L   G   L   P   W   F   E
       810              820              830              840

-----T-------A--T-----------N--E-------T
 E   S   L   L   E   E   F   I   S   R   P   P
AAGAGTCATTACTTGAAGAATTCATTCTCGCGCCCCCGCCC
  |     |||||     ||   ||     |||     ||   |   ||     |||
ATACATCTTTGGCCCACAACGTTTATAAACGAACCTCGTAC
 E   S   L   L   E   E   F   I   S   R   P   P
       850              860              870              880

---..D--Y--R---G--S-----V--S-----H--H------
 V   I   C   S   R   T   R   M   P   L   D   R   T
TGTTATTTGTTCGAGAACTCGAATGCCGCTGGACCGAACT
  |     |   ||||     |||||   ||||   ||     ||||||
TG...ATTATCCGCGGTAGTAGGGTGTCATTACACCATACG
 V   I   C   S   R   T   R   M   P   L   D   R   T
       890              900              910              920
```

*FIG. 5G*

```
         ----------R------|                                       |
L  L  A  I  F  K  R  K  E  L  C  S  E  N
CTCCTGGCCATTTTTAAACGGAAAGAGCTGTGTAGCGAAA
|||  ||| ||||| ||||||   | |  |||     |
CTTTTAGCGATATTTAAGCGGCGAGAATTATGT
        930        940        950        960

G  E  L  L  T  Q  Y  S  W  I  L  W  G
ATGGGGAGCTGTTAACTCAGTATTCTTGGATATTGTGGGG
        970        980        990       1000

L  L  T  K  L  H  T  I  N  V  E  L  F
ATTACTGACTAAACTACACACCATTAATGTCGAATTATTT
       1010       1020       1030       1040

|---V--E--L--L
D  I  S  G  M  S  R  R  E  C  A  S  A  I
GACATTAGCGGTATGTCACGTCGAGAATGCGCCAGCGCTA
       1050       1060       1070
                                 ||      |
                                 TGTGTAGAACTGC
                                        1080

FIG. 5H
```

```
     -D------S---------V--H--S---
      M  H  T  M  P  E  R  L  S  T  L  A  S
     TAATGCATACTATGCCGGAGAGATTGTCTACTCTCGCTAG
      ||||| |||||||||| ||||||||| |||||| |||||
     TTATGGATACTATGTCGGAGAGATTGGTAACACATAGTAG
           1090           1100           1110           1120

---A--F----I-----A------L--A--
      W  N  D  L  C  E  L  E  D  D  V  I  S
     CTGGAATGATTTATGCGAGCTTGAAGATGATGTAATTTCC
     ||||||| || |||| ||||| |||| ||||||| |||||
     CTGGAATGCCTTCGAGATTGAAGCTGATGTACTAGCC
           1130           1140           1150           1160

---E----A--M---*|
      Y  N  K  G  M  C  N  E  V  G  A  S  R  *
     TATAATAAGGGAATGTGTAACGAGGTTGGAGCGTCTCGAT
     |||||||||  ||||  ||||
     TATAATAAAGAGAGATGGCTATGTAA
           1170           1180           1190           1200

AATTCTTCTTAATCTGCTGGTATTGGTTACTGCCATAACT
           1210           1220           1230           1240
```

FIG. 5I

TATTATTGGTCCATGCTAGAATAGTCATACGCTACGATCT
1250        1260        1270        1280
GTTGCTATATATGACTATCGCCAAACTGTTAAACCCGCGA
1290        1300        1310        1320
AGAATATATTTCATATAAACCTAAGGGCCCCTCAGTCTGA
1330        1340        1350        1360
TTTTTTGTGAAAACGTGTATACCA
1370        1380

```
  1 CAGCTGCCTATGTAGTGAAATCTATACTGGATTT
    ATCATAACTAGTTTACTTGTTGTATATTAGTAGCGCTATCT
    TGACCAAATCGTTGTTCACATCTTGGCCATATACGTATTGATC
121 GTTGTTTCGAACCGCGAATAAAACTTTCATACATAC
    TAAACGATGGAGTTGTGTTTTATGAGCGTTGAAAACAAAGGT
    ACCATCGGTTTAAAACTAAGTTGCATATCGTAATCCACAAAA
241 ATCATTTTATACATCATCCCGAAGAGACACCAAACG
                                    M  L  T  P  R  V
    TAACCCTCTACATATCTTCCCCATGCTCACGCCGTGTGT
     L  R  A  L  G  W  T  G  L  F  F  L  L  L  S
    TACGAGCTTTGGGGTGGACTGGACTCTTTTTTTGCTTTTAT
         P  S  N  V  L  G  A  S  L  S  R
361 CTCCGAGCAACGTCCTAGGAGCCCTAGCCCTTAGCCGG
     D  L  E  T  P  P  F  L  S  F  D  P  S
    GATCTCGAAACACCCCCATTTCTATCCTTTGATCCATCCA
```

FIG 6B

```
        N   I   S   I   N   G   A   P   L   T   E   V   P   H   A   P
     ACATTTCAATTAACGGGGCGGCCCTTTAACTGAGGTACCTCATGCAC

S   T   E   S   V   S   T   N   S   E   S   T
481  CTTCCACAGAAAGTGTGTCAACAATTCGGAAGTACC

N   E   H   T   I   E   T   T   G   K   N   A   Y
     AATGAACATACCATAACAGAAACGACGGGCAAGAACGCATACA

I   H   N   A   S   T   D   K   Q   N   A   N   D
     TCCACAACAATGCGTCTACGGACAAGCAAAATGCGAACG

T   H   K   T   P   N   I   L   C   D   T   E
601  ACACTCATAAAACGCCCAATATACTCTGCGATACGGA

E   V   F   F   L   N   E   T   G   R   F   V   C
     AGAAGTTTTTGTTTTCCTTAACGAAACGGGAAGATTTGTTTGT

T   L   K   V   D   P   P   S   D   S   E   W   S   N
     ACTCTCAAAGTCGACCCCCCCTCGGATAGTGAATGGTCCA

F   V   L   D   L   I   F   N   P   I   E   Y
721  ACTTTGTTCTAGATCTTGATCTTTAACCCAATTGAATA

H   A   N   E   K   N   V   E   A   A   R   I   A   G
     CCACGCCAACGAAAAGAATGTGGAAGCGGCGTATCGCTGGT
```

```
      L  Y  G  V  P  G  S  D  Y  A  Y  P  R  Q
      CTCTATGGAGTCCCCGGATCAGACTATGCATACCCACGTC
                  S  E  L  I  S  S  I  R  R  D  P
  841 AATCTGAATTAATTTCTTCGATTCGACGAGATCCCC
      Q  G  T  F  W  T  S  P  S  P  H  G  N  K
      AGGGCACATTTTGGACGAGCCCATCACCTCATGGAAACAA
      Y  F  I  W  I  N  K  T  N  T  M  G  V  E
      GTACTTCATATGGATAAACAAAACAACCAATACGATGGGGTGG
                  I  R  N  V  D  Y  A  D  N  G  Y
  961 AAATTAGAAATGTAGATTATGCTGATAATGGCTAC
      M  Q  V  I  M  R  D  H  F  N  R  P  L
      ATGCAAGTCATTATGCGTGACCATTTTAATCGGCCTTTAA
      I  D  K  H  I  Y  I  R  V  C  Q  R  P  A  S  V
      TAGATAAACATATTTACATACGTGTGTGTCAACGACCTGCATCAG
                  D  V  L  A  P  P  V  L  S  G  E  N
 1081 TGGATGTACTGGCCCCTCCAGTCCCTCAGGGGAGAAAA
      Y  K  A  S  C  I  V  R  H  F  Y  P  P  G
      TTACAAGGCATCTTGTATCGTGTTAGACACTTTTATCCCCCTGGA
```

*FIG. 6C*

```
      S   V   Y   V   S   W   R   Q   N   G   N   I   A   T
      TCTGTCTCTATGTATCTTGGAGACAGAATGGAAACATTGCAA
                P   R   K   D   R   D   G   S   F   W   F
1201  CTCCTCGGAAAGATCGCGATGGAAGTTTTGGTGGTT
      E   S   G   R   G   A   T   L   V   S   T   I   T   L
      CGAATCTGGTAGAGGAGCTACGTTGGTTTCTACAATAACATTG
      G   N   S   G   I   D   F   P   P   K   I   S   C   L
      GGAAATTCAGGAATTGATTTCCCCCCAAAATATCTTGTC
                V   A   W   K   Q   G   D   M   I   S   T   T
1321  TGGTTGCCTGGAAGCAGGGTGATATGATCAGCACGAC
      N   A   T   A   I   P   T   V   Y   H   H   P   R   L
      GAATGCCACAGCTATCCCGACGGTATATCATCATCCCCGTTTA
      S   L   A   F   K   D   G   Y   A   I   C   T   I   E
      TCCCTGGCTTTTAAAGATGGGTATGCAATATGTACTATAG
                C   V   P   S   E   I   T   V   R   W   L   V
1441  AATGTGTCCCCTCTGAGATTACTGTACGGTGGTTAGT
      H   D   E   A   Q   P   N   T   T   Y   N   T   V   V
      ACATGATGAAGCGCAGCCTAACACAACTTATAATACTGTGGTT
```

*FIG. 6D*

```
     T  G  L  C  R  T  I  D  R  H  R  N  L  L
     ACAGGTCTCTGCCGACCATCGATCGCCATAGAAATCTCC

S  R  I  P  V  W  D  N  W  T  K  T
1561 TCAGCCGCCATTCCAGTATGGGACAATTGGACGAAAAC

K  Y  T  C  R  L  I  G  Y  P  F  D  E  D
     AAAATATACGTGCAGACTCATAGGCTACCCCTTCGATGAAGAT

K  F  Q  D  S  E  Y  Y  D  A  T  P  S  A
     AAATTCAAGATTCGGAATATTACGATGCAACTCCATCTG

R  G  T  P  M  V  I  T  V  T  A  V
1681 CAAGAGGAACACCCATGGTTATTACGGTTACGGCAGT

L  G  L  A  V  I  L  G  M  G  I  I  M  T
     TTTGGGATTGGCTGTAATTTTAGGGATGGGGATAATCATGACT

A  L  C  L  Y  N  S  T  R  K  N  I  R  L
     GCCCTAGTGTTTATACAACTCCACACGAAAAATATTCGAT

*
1801 TATAATCTCATTGTTATGTAGTTGTGATTTATTAAAC

ATATTTTTATAACTCTAGTATTCCCGAGTACTTATATATT
```

FIG. 6E

TATTTGTCAGACAATAATGCAATAGTGGAGAAACGTGAGG

1921 GGAGTCTGTAAACAGAATACGTATAATCATCTATTTG

AATAAAGATTGTGGTATAAATGAAGATAGCGCAAGTCATTC

CAAGCTCTCCATTCTATTTAAACAATGTACAGTTTAAAGT

FIG. 6F

HVT HOMOLOGUES OF VZV62/ HSV-1 IE 175

```
 S  N  V  V  R  Y  M  C  G  N  T  V  L
TCGAATGTGGTGCGATACATGTGCGGGAACACGGTACTCC
         10        20        30        40

P  P  D  P  H  G  T  P  V  V  I  N  V  P
CCCCGGATCCCCATGGCACCCCCGTGGTGATCAACGTTCC
         50        60        70        80

E  G  T  S  E  T  M  A  E  L  T  V  A
CGAGGGAACGTCCGAAACTATGGCGGAGCTTACTGTTGCT
         90       100       110       120

H  V  G  R  K  S  I  G  W  P  T  S  E
CACGTTGGGCGCAAGTCTATTGGGTGGCCGACCTCCGAGT
        130       140       150       160

W  H  S  A  T  I  L  Q  K  D  N  D  S  R  L  V  I  I  R
GGCATTCCGCTACAATCCTGCAGAAAGATAATGATAGTCGGCTGGTAATTATACGCC
        170       180       190       200       210
```

HVT HOMOLOGUE OF RIBONUCLEOTIDE
REDUCTASE (LARGE SUBUNIT)

```
 Q  V  T  E  V  S  E  G  F  A  P  L  F
CAAGTGACCGAGGTTAGCGAAGGATTTGCCCCTTTGTTCA
         10        20        30        40

S  N  M  F  S  K  V  T  S  A  G  E  L  L
GTAACATGTTCAGCAAGGTGACAAGTGCCGGGGAACTGCT
         50        60        70        80

R  P  N  S  Q  L  M  R  E  L  R  Q  I
TAGACCCAACAGTCAATTAATGCGGGAGCTGAGACAAATA
         90       100       110       120

Y  P  D  N
TATCCCGATAAT
        130
```

MDV HOMOLOGUE OF RIBONUCLEOTIDE
REDUCTASE (LARGE SUB-UNIT)

```
 G  I  M  E  G  S  D  V  P  T  E  K  S
GGGGATAATGGAAGGAAGTGATGTACCGACGGAAAAATCT
         10        20        30        40

H  S  G  R  E  R  N  R  S  M  G  I  G
CATTCTGGCCGAGAACGTAACAGATCGATGGGCATCGGCG
         50        60        70        80

V  Q  G  F  H  T  A  F  L  S  M  G  L  D
TGCAGGGCTTTCATACAGCTTTTCTATCTATGGGTCTTGA
         90       100       110       120

L  C  D  E  R  A  R  S  L  N  K  L  I
TTTATGCGATGAACGCGCTAGATCCCTCAACAAGCTAATT
        130       140       150       160

F  E  F  M  L  L  E  A  M  T  V  S  C
TTTGAATTCATGTTATTGGAGGCGATGACAGTTAGTTGCG
        170       180       190       200

E  F  C  E  R  G  L  P  P  F  A  D  F  S
AATTCTGCGAACGAGGCCTGCCGCCGTTTGCTGATTTCTC
        210       220       230       240
```

FIG. 9A

```
N   S   Y   Y   A   R   G   R   L   H   F   D   G
TAACAGTTATTATGCACGAGGACGTCTGCATTTCGATGGG
         250         260         270         280

W   A   N   V   E   L   A   A   V   E   E   W   N
TGGGCTAATGTAGAATTGGCTGCAGTGGAAGAGTGGAATA
         290         300         310         320
```

FIG. 9B

MDV HOMOLOGUE OF RIBONUCLEOTIDE
REDUCTASE (SMALL SUB-UNIT)

```
          L   D   V   E   A   I   L   C   Y   V   R   Y   S
          TATTGGATGTTGAAGCAATATATTATGTTACGTTACAG
                      10          20          30          40

R   G   Q   T   E   R   I   D   M   P   P   I
          CCGCGGACAGACTACTGAAAGAATAGATATGCCACCTATT
                  50          60          70          80

Y   N   E   P   K   P   T   A   D   F   P   H   A   L
          TACAACGAACCTAAACCTACAGCTGATTTTCCGCATGCAC
                  90         100         110         120

T   A   S   N   N   T   N   F   F   E   R   R   N
          TGACAGCTTCAAATAATACCAACTTCTTTGAGAGAAGAAAA
                 130         140         150         160

T   A   Y   S   G   S   V   S   N   D   L   *
          TACTGCATACTCTGGAAGCGTGTCAAACGATCTTTAA
                 170         180         190
```

FIG. 10

MDV HOMOLOGUE OF HSV-1 IE-175

```
    P   I   P   Y   V   E   E   M   K   D   Y   A
CCCATTCCCGTCTATGTAGAGGAAATGAAAGATTATGCCA
           10          20          30         40

K   Q   Y   D   A   L   V   N   S   L   F   H   K   S
AACAATACGACGCTCTCGTAAACTCTTTGTTTCACAAAAG
           50          60          70         80

M   K   V   N   P   L   N   W   M   H   H   G   K
CATGAAAGTAAATCCTCTGAACTGGATGCACCACGGGAAG
           90         100         110        120

L   S   T   A   D   A   A   L   N   H   I   Y   V
CTGTCTACCGCCGATGCTGCCCTAAACCACATATATGTTC
          130         140         150        160

Q   K   F   Q   S   S   Y   D   S   P   G   A   A   V
AGAAATTCCAGAGTTCATACGATTCGCCCGGAGCGGCTGT
          170         180         190        200

T   G   T   V   N
AACTGGCACAGTTAACA
          210
```

FIG. 11

MDV HOMOLOGUE OF HSV-1 IE-68

```
  S  D  Q  D  F  E  L  N  N  V  G  K  F
CGTCCGATCAAGACTTTGAACTTAATAATGTGGGCAAATT
        10        20        30        40

C  P  L  P  W  K  P  D  V  A  R  L  C
TTGTCCTCTACCATGGAAACCCGATGTCGCTCGGTTATGT
        50        60        70        80

A  D  T  N  K  L  F  R  C  F  I  R  C  R
GCGGATACAAACAAACTATTTCGATGTTTTATTCGATGTC
        90       100       110       120

L  N  S  G  P  F  H  D  A  L  R  R  A
GACTAAATAGCGGTCCGTTCCACGATGCTCTTCGGAGAGC
       130       140       150       160

L  F  D  I  H  M  I  G  R  M  G  Y  R  L  N
ACTATTCGATATTCATATGATTGGTCGAATGGGATATCGACTAAA
       170       180       190       200
```

```
              10         20         30         40         50         60         70         80         90
MDV  AATGTCTTTTGAAGTCGAGCCCAATCGAAACCATATTTTGTCTGCTATCAGAACTGCAAGTCTCGTTGACAGATGCTCCAAATAAGTG
      T  K  Q  L  R  A  W  D  F  G  Y  K  Q  R  S  D  S  S  A  L  R  T  S  L  H  E  L  Y  T 100        110        120        130        140        150        160        170        180
MDV  GGAACCGACTCAATCGCACTCATAAAGTTAGTGGGATGAGAAATATTAGTCCCAGTTTTTGCATAGAATGCATATAAACAAAGAATCGCA
      P  V  S  E  I  A  S  M  F  N  T  P  H  S  I  N  T  G  T  K  A  Y  F  A  Y  L  C  L  I  A 190        200        210        220        230        240        250        260        270
MDV  CATTCTAGAGAGGAATAATAACGGGTGCCTACATATAAACGTCCGCATGATTGTAAAGATGTGATTGCCGTCACAATAAACGTTCGCGAC
      C  E  L  S  S  Y  Y  R  T  G  V  Y  L  R  G  C  S  Q  L  S  T  I  A  T  V  I  F  T  R  S 280        290        300        310        320        330        340        350        360
MDV  ATTCTTCCACCATGATAGTCTATTTTTCTGGCAACGCTGTGGGCTTGTCTGTGCAACCAGAGCATTTGTAAAGTACGATACCACGTGCCGAAA
      M  R  G  G  H  Y  D  I  K  R  A  V  S  P  K  D  V  A  L  A  N  Q  L  T  R  Y  W  T  G  F 370        380        390        400        410        420        430        440        450
MDV  ACGACACCGGAGTTCACTACTACATTCCTATTTGCATAGACAAATTAGAGTCGTATCTGAGCAAAGGATCA
      V  V  G  S  N  V  V  N  R  N  A  Y  V  L  N  L  L  D  V  S  L  N  S  D  Y  R  L  L  P  D 460        470        480        490        500        510        520        530        540
MDV  TTTTTCACGATTTGAATCTCACGGGCCGAAGTGATATTAACGTCTTCCTTGTGCTGTTCCAGATTTTCAACAGCACTAACGGCAATATCC
      N  K  V  I  Q  I  E  R  A  S  T  I  N  V  D  E  K  H  Q  G  S  K  E  V  A  S  V  A  I  D 550        560        570        580        590        600        610        620        630
MDV  ATTGCAGCGTCGGCAAGTTCTGCTGCAGCCCGCTAACGCGCTGTTGCAGATATTCAATTTTTTCTTCTTATTGGT
      M  A  A  D  A  L  E  A  A  A  A  H  E  L  D  A  L  A  T  A  I  Y  E  I  K  E  E  I  P
```

*FIG. 14A*

```
      640       650       660       670       680       690       700       710       720
MDV   CGAAGTCTGCGGTCAATTTCTATTGCAATAGAGTCGGTATGACCATCCAAATTATTTAATGCTGCAGTGGCGGCATTGTTTCGTGCAGTA
      R  L  R  R  D  I  E  I  A  I  S  D  T  H  G  D  L  N  N  L  A  A  T  A  A  N  N  R  A  T 730       740       750       760       770       780       790       800       810
MDV   ATGATCGCAAGTTGTCGTTCCATATTGGCGCGGTTAGATGTAAATACCGGTTCCTTCCAGAACTCGATGGGCCATGGGGGAGCTATAAAG
      I  I  A  L  Q  R  E  M  N  A  R  N  S  T  F  V  P  E  K  W  F  E  I  P  W  P  P  A  I  F 820       830       840       850       860       870       880       890       900
MDV   TTCTTCACATCGGCAGGGAACATTTCCATTCCATCGCCTGTCAATATTCTCGCGTCCCAAATAAAGTTTGCCATGATGGTGCTACTCGAT
      N  K  V  D  A  P  F  M  E  M  G  D  G  T  L  I  R  A  D  W  I  F  N  A  M 910       920       930       940       950       960       970       980       990
MDV   ATAATCAGACAGAAGTTACAGGGAAACGCCACATGAGAAAATAATACTACATTTAAACTACACAAGCTTATAAAAGTGTTACGGTCTCTG
                                                                                 .  P  R  Q 1000      1010      1020      1030      1040      1050      1060      1070      1080
MDV   AACAAGACGGGCGATAATATTAGCCATGTTTCGCATAGCCGTACCTCCCGTTCTCTCCTGATTATTTGAAAATGATAAAGTAGCCGTTTT
      V  L  R  A  I  I  N  A  M  N  R  M  A  T  G  G  T  R  E  Q  N  N  S  F  S  L  T  A  T  K 1090      1100      1110      1120      1130      1140      1150      1160      1170
MDV   ATTACAAGCTATATGATTCCTCAAATCCGTTACGTTAGCAGACGCCTTTCCACTGCGTCGTTGTATATGTATCGTGTTTGTATTATGACG
      N  C  A  I  H  N  R  L  D  T  V  N  A  S  A  K  G  S  R  R  Q  I  H  I  T  N  T  N  H  R 1180      1190      1200      1210      1220      1230      1240      1250      1260
MDV   TTTTAAAATTTTATGAGTGTCAGTTATCCGTGCTTTATAGTCAGACGCGGTCGCCAATATAGAGCATAGTCTATGAAAATCAGTCACTAT
      K  L  I  K  H  T  D  T  I  R  A  K  Y  D  S  A  T  A  L  I  S  C  L  R  H  F  D  T  V  I 1270      1280      1290      1300      1310      1320      1330      1340      1350
```

FIG. 14A-1

```
MDV       G    TTTTCTTTTAGGCACATCACATGTAGAACAGAGTTTCGTCTTGCTACAAATACTAACATTGGACAAATAACGATACAATCTGA
       H  R  K  K  L  C  M  V  H  L  V  S  L  K  R  R  A  V  F  V  L  M  P  C  I  V  I  C  D  S
             1360      1370      1380      1390      1400      1410      1420      1430     1440

MDV    TCCTTGAGGCGCAATTGCCCAATCAGAGATTTGGAATCCAATAACTGCTTGTTGTTCATGTTCTTTGTTACTGCGTGTCTT
        G  Q  P  A  I  Q  G  I  L  S  K  S  D  L  L  Q  K  I  G  T  L  R  Q  E  H  K  S  R  T  K
             1450      1460      1470      1480      1490      1500      1510      1520     1530

MDV    CAGGTTACGAGAAAAATTGCAAGTTTTAGTTCTAGAATGACGCATACTCCATCACAAATCACCAGGCAACTTAAA
        L  N  R  S  F  K  C  T  K  L  E  L  I  V  C  V  G  D  C  G  V  E  W  L  D  R  P  L  K  F
             1540      1550      1560      1570      1580      1590      1600      1610     1620

MDV    CATGCAAATACAATCCGTGTTCTACGTCTAGTTTTACTTCGAAGACCAATCGTCAACTGTTTAAATACATCTAATACCAT
        M  C  I  C  D  D  P  P  R  R  R  E  L  N  V  E  F  V  L  R  F  D  T  L  Q  K  F  V  D  L  V  M

MDV        V  K  G  F  F  I  K  A  F  S  R  G  P  W  D  Y  V  Q  S  G  L  C  M  A  E  A  Y  ---R---  L  K  K  Y
HVT                                                                                    ::::

HVT                                                                                                                        AAGCTTTTTGTA
                                                                                                                           :::: ::

MDV    GACCTTCCCAAAAATTTGGCAAAGCTTCTCCCCGGCCAATCATACACCTGAGATCCTAGACACATCGCTTCTGCATAAAGCCGTTTGTA
        F  R  N  H  G  R  V  G  A  K  L  L  G  A  M                 F  N  R  T  S  S
HVT    ---------D-----C---------A-----R--R--K--R--L  V  N  T  N  V  H  R  K  F  N  R  T  S  S
                                                              :::: ::::
             1630      1640      1650      1660      1670      1680      1690      1700     1710

MDV    AAAACGATTATGACCACGGAGACACCCGAATCCTGCCATAAGGTGTT..........TCCCGCGTGCTTGCCTGCGAAGACAAT
HVT    ::::  ::::                :::: :::: ::                    :::: ::::  ::::
             1720      1730      1740      1750      1760      1770      1780      1790     1800

MDV    AAGCGATCGTGACATCGAACATCCAGCCGCTAAACGTGCTTTCTAAGGACATTGCGTATTTACATGCCGTTTGAAATTTCGAGTGCTACT
HVT    :::: ::::  :::: ::::   :::: ::::                              ::::
```

```
        :::  : :   :: ::   ::   : ::: :      :      :
MDV  ATTCCCTCGGACCGATCTGGTCTTAAATTAGATGACAAAGAGGATCCTCTAGAT
           3520      3530      3540      3560      3570      3580      3590      3600      3610

L  N  P  G  Y  K  F  V  L  T  S  E  L  V  G  A  Y  T  K  R  S  C  F  V  D  P  M  D  S  L
HVT  CTCAACCCCGGATACAAGTTCGTTCTCACAAGCGAGTTGGTAGGAGCCTACACAAAACGATCTTGTTTTGTCGATCCGATGGATTCTCTC
           3620      3630      3640      3650      3660      3670      3680      3690      3700

V  P  I  D  Y  D  H  V  R  T  I  I  F  G  S  A  G  M  E  I  L  M  K  M  G  I  T  L  A  S
HVT  GTCCCGATAGATTATGATCATGTACGAACCATTATATTCGGATCTGCTGGGATGGAGATTTTAATGAAGATGGGAATTACTTTGGCATCT
           3710      3720      3730      3740      3750      3760      3770      3780      3790

M  T  I  S  T  K  Y  N  P  P  I  E  L  I  I  S  A  K  Y  R  N  L  S  L  L  W  P  P  R  Q
HVT  ATGACCATTTCGACGAAATATAATCCTCCTATTGAACTGATAATATCTGCAAAGTACCGAAATTTATCACTGTTGTGGCCACCCCGACAA
           3800      3810      3820      3830      3840      3850      3860      3870      3880

Q  Y  E  P  V  N  K  G  T  G  R  P  H  W  I  Y  L  L  G  V  Y  R  N  V  S  D  S  E  R  D
HVT  CAATATGAACCTGTAAATAAAGGGACTGGACGCCCCCATTGGATCTACCTATTAGGTGTGTATAGAAACGTTTCGGACTCCGAGCGTGAC
           3890      3900      3910      3920      3930      3940      3950      3960      3970

S  Y  M  N  M  I  K  S  L  G  D  S  M  D  Y  H  F  L  I  S  R  A  H  A  Q  M  L  I  L  A
HVT  TCATACATGAATATGATTAAGAGTCTGGGCGATTCTATGGATTATCACTTCCTAATTAGCAGAGCGCATGCCCAGATGCTGATACTGGCA
           3980      3990      4000      4010      4020      4030      4040      4050      4060

A  E  D  R  L  V  D  E  M  H  S  F  R  N  V  I  A  R  L  F  V  S  L  F  A  F  I  R  N  A
HVT  GCAGAGGACCGGCTCGTGGATGAAATGCATAGTTTCAGGAACGTTATTGCGCGTTTATTTGTATCGTTGTTCGCATTCATACGTAACGCA
           4070      4080      4090      4100      4110      4120      4130      4140      4150

F  Q  S  G  Y  T  S  L  N  D  I  I  E  I  E  A  D  L  R  L  I  V  E  G  I  S  S  A  A  F
HVT  TTTCAGTCTGGCTACACCTCTCTTAATGACATAATTGAAATCGAAGCCGATTTGAGGTTAATTGTAGAAGGCATTTCTTCTGCTGCATTT
           4160      4170      4180      4190      4200      4210      4220      4230      4240
```

FIG. 14E

```
       R  K  D  A  S  T  H  F  L  I  S  G  T  P  I  K  D  S  K  A  D  L  I  K  S  L  L  S  K  V
HVT  CGTAAAGACGCTAGTACACACTTTCTTATATCGGGACGCCCATAAAGATAGCAAAGCGGATTTAATTAAATCGTTGTTGTCTAAAGTC
          4250         4260         4270         4280         4290         4300         4310         4320         4330

I  R  P  I  S  G  H  T  R  P  L  S  A  I  Q  H  L  F  L  L  R  S  A  Y  A  L  D  I  P  R
HVT  ATTCGACCAATTTCCGGACACATACACGTCCCTTATCTGCAATACAACATCTATTCCTTTTGAGATCCGCTTATGCATTGGATATACCCCGT
          4340         4350         4360         4370         4380         4390         4400         4410         4420

Q  N  G  S  L  S  E  Q  V  S  T  V  A  L  S  F  I  E  N  I  H  S  E  A  M  R  D  I  L  S
HVT  CAAAACGGATCTTTGAGGCAACAGGTATCTACACTGGCACTGTCGTTCATTGAAAATATTCACAGCGAGGCCATGAGGGACATTCTGTCA
          4430         4440         4450         4460         4470         4480         4490         4500         4510

W  N  T  T  K  H  A  L  Y  Y  A  F  A  S  I  L  Q  R  P  L  T  E  W  G  A  S  R  N  A
HVT  TGGAACACTACAACAAAGCATGCGTTGTATTATGCCGAGTATTTGCAACGGCCACTGACCGAATGGGGCGCCTCAAGAAATGCA
          4520         4530         4540         4550         4560         4570         4580         4590         4600

R  R  A  I  L  L  A  S  S  M  C  T  E  E  H  V  I  A  T  E  L  A  I  Q  E  L  Y  V  K  I
HVT  CGGAGGGCAATACTATTAGCATCATGATGTGTACAGAAGAGCATGTTATCGCAACTGAGTTGGCTATTCAAGAACTGTATGTCAAAATC
          4610         4620         4630         4640         4650         4660         4670         4680         4690

R  S  N  A  D  P  I  H  L  L  D  V  Y  T  P  C  L  S  S  L  R  L  D  L  S  E  H  H  R  I
HVT  AGAAGTAATGCCGACCCAATACACCTTCTAGACGTATATACCACCATGTCTTTCTTCACTACGATTGGACCTTTCCGAACACCATCGGATA
          4700         4710         4720         4730         4740         4750         4760         4770         4780

Y  A  M  A  D  V  V  F  Y  P  D  I  Q  Q  Y  L  K  K  K  S  H  E  G  N  M  K  E  D  D  L
HVT  TACGCAATGGCAGATGTAGTTTTCTATCCAGACATTCAGCAGTATTTGAAAAAAAAATCCATGAGGGTAATATGAAGGAAGATGATCTC
          4790         4800         4810         4820         4830         4840         4850         4860         4870
```

*FIG. 14E-1*

```
      E T K A E Y I L T K L R S P L I R T L S A Y A S E V L S C S
HVT  GAAACAAAGGGCGGAATACATCCTCACCAAGCTTAGGTCGCCGTTGATCAGAACGCTGTCTGCTATGCCTATGCATCAGAAGTATTGTCCTGCTCC
              4880          4890          4900          4910          4920          4930          4940          4950          4960

D Q D L E I N A I L I L P V S G I G S Y V V S R R A G M Q
HVT  GACCAGGATCTATTAGAATAAATGCTATTTTAATTCTGCCCGTTTCCGGTATTGGGAGCTATGTAGTCTCTCGAAGGGCAGGAATGCAA
              4970          4980          4990          5000          5010          5020          5030          5040          5050

G I V Y T V D G V D V N N Q L F I T Y T R M P C T T I G N
HVT  GGCATTGTTTATACCGTAGACGGTGTTGATGTTAACAATCAGCTTTTTATAACATATACCAGAATGCCGTGCACTACAACGATAGGTAAC
              5060          5070          5080          5090          5100          5110          5120          5130          5140

I V P T V L S R P S G K T C P Y C G C V L R Y S A D G N I
HVT  ATTGTTCCAACAGTATTGTCAAGACCCTCGGGAAAAACGTGTCCGTATTGCGGCTGTGTTTTGCTGCCGATATTCCGCCGATGGAAATATC
              5150          5160          5170          5180          5190          5200          5210          5220          5230

R Y S I Y I S S
HVT  CGCTATTCTATTTACATTTCGTCCC
              5240          5250
```

*FIG. 14F*

```
G R R K Y D A L V A - F V L G R A C G R P I Y L R E
GGGACGACGCAAATATGATGCTCTAGTAGCAT4GTTTGTCTTGGGCAGAGCATGTGGGAGACCAATTTATTTACGTGAA

Y A N C S T N E P F G T C K L K S L G W D R R Y A
TATGCCAACTGCTCTACTAATGAACCATTTGAACTTGTAAATTAAAGTCCCTAGGATGGTGGGATAGAAGATATGCAA

M T S Y I D R D E L K L I A A P S R E L S G L Y T R
TGACGAGTTATATCGATCGAGATGAATTGAAATTGATTATTGCAGCACCCAGTCGTGAGCTAAGTGGATTATATACGCG

L I I N G E P I S S D I L L T V K
TTTAATAATTATTAATGGAGAACCCATTTCGAGTGACATATTACTGACTGTAAA
```

FIG. 15

VIRAL VACCINES

This is a division of application Ser. No. 08/654,931 filed May 29, 1996, Pat. No. 5,794,143; which is a divisional of Ser. No. 08/462,591 filed Jun. 5, 1995; which is a divisional of Ser. No. 08/081,932 filed Jun. 23, 1993, Pat. No. 5,558,860; which is a CIP of Ser. No. 07/669,392 filed on Apr. 29, 1991 (now abandoned).

BACKGROUND OF THE INVENTION

1. Field of the Invention

The present invention relates to viral vaccines which may be used to provide immunity against disease and to nucleotide sequences for inclusion in such vaccines.

2. Description of Related Art

Herpesviruses are large double stranded DNA viruses consisting of an icosahedral capsid surrounded by an envelope. The group has been classified as alpha, beta and gammaherpesviruses on the basis of genome structure and biological properties [Roizman, B. et al. (1981) Intervirology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis Virus (ILTV) (an alphaherpesvirus) which causes an acute upper respiratory tract infection in chickens resulting in mortality and loss of egg production.

A recent unexpected finding in our laboratory is that there is sufficient amino acid homology between MDV, ILTV and mammalian herpesviruses, particularly varicella zoster (VZV) and Herpes Simplex Virus (HSV) to allow identification of numerous conserved genes. These include the MDV and Herpesvirus of Turkeys (HVT) homologues of glycoproteins gB, gC and gH of HSV: the ILTV, MDV and HVT homologues of TK and ribonucleotide reductase genes and the ILTV homologue of gB and genes 34 and 35 of VZV [Buckmaster, A. et al (1988) J. gen. Virol, 69, 2033–2042].

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic. These observations and the fact that there are MDV type-specific epitopes that are not shared by HVT or type 2 MDV have led us to the conclusion that improved vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 13–31, Macmillan, 1986].

A number of herpesvirus antigens have been shown to confer protective immunity when expressed in a recombinant vaccinia virus. These include the gB gene of HSV [Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpesviruses, gB and its homologues are important immunogens. Moreover, the presence of gB at the surface of infected cells has been shown to be an important target for humoral and cell-mediated immune responses [Blacklaws, B. A. et al J.gen. Virol. 68, 1103–1114 (1987); McLaughin-Taylor, E. et al (1988) J. gen. Virol. 69, 1731–1734]. The recently described glycoprotein gH of HSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T⁻ cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV [Shih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TX-virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragment of HSV TK and the recombinant was introduced into the PRV mutant by homologous recombination. TK– virus was selected which expressed the human gene (Thomsen et al as above). Similarly, VZV has been used as a vector [Lowe et al (1987) Proc. Natl. Acad. Sci. U.S.A. 84, 3896–3900]. Several herpesvirus genes have also been shown to be associated with virulence and to be non-essential for growth in vitro. These include the TX genes of HSV (Jamieson, A. T. et al (1974) J. gen. Virol. 24, 465–480; Field, H. and Wildy, P., (1987) J. Hygiene (Cambridge) 81, 267–277] and of PRV. Indeed it has long been known that PRV is readily attenuated by deletion of TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity (Rosen, A. et al (1986) Virus Research 5, 157–175; Thompson, R. L. et al (1983) Virology 131, 180–192]. Several additional genes of HSV have been shown to be non-essential for growth in vitro although it is not known whether they are associated with virulence. These include UL24 [Sanders, P. G., (1982), J. gen. Virol. 63, 277–295], large subunit of ribonucleotide reductase [Goldstein D. J. and Weller, S. K. (1988) J. Virol. 62, 196–205], gC [Draper K. G. et al (1984) J. Virol. 51, 578–585], dUTPase [Fisher, F. B. & Preston, V. G. (1986,) Virology 148, 190–197], and $U_L$ 55 and $U_L$ 56 [MacLean, A. R. & Brown, S. M. (1987) J. gen. Virol. 68, 1339–1350]. Moreover there is evidence that several genes of HSV mapping in $U_s$ are also non-essential for growth in vitro [Weber, P. C. et al (1987) Science 236, 576–579].

WO 88/07088 (published only on Sep. 22, 1988) disclosed hybrid viral vectors based on HVT or MDV and including a gene of interest in a non-essential site, such as the TK region or the region encoding protein A. Protein A, in this context, appears to be the same as gC, disclosed by Velicer and Coussens [Coussens, P. M. & Velicer, L. F. (1988) J. Virol. 62, 2373–2379].

SUMMARY OF THE INVENTION

One aspect of the present invention provides a nucleotide sequence substantially free of the sequences which would adjoin it in the wild-type virus associated with the sequence, the sequence being selected from the group consisting of:

(a) the MDV homologue of the HSV gB gene, (b) the MDV homologue of the HSV gH gene, (c) the TK gene of MDV, (d) the MDV homologue of the immediate early gene IE-175 of HSV-I, (e) the MDV homologue of the immediate early gene IE-68 of HSV-I, (f) the MDV homologue of the HSV gD gene, and minor variations thereof.

In addition, the TK sequence of HVT, referred to hereinafter sometimes as sequence (x), and the MDV analogue of HSV gC, referred to hereinafter sometimes as sequence (y), and minor variations of either may be used as insertion sites for certain heterologous sequences or as deletion sites to obtain less virulent viruses but are not novel per se.

Each of sequences (a) to (f), (x) and (y) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (d) and (f) above.

The term "minor variations thereof" is intended to include changes in the nucleotide sequences which do not affect the essential nature of the nucleotide sequences or the proteins encoded by them, for example, minor substitutions of nucleotides for one another. In the case of sequences which are intended for insertion into a vector to encode an antigen, the "essential nature" of the sequence refers to the protein or glycoprotein encoded. Conservative changes in the nucleotide sequences which give rise to the same antigen will clearly be included, as will changes which cause conservative alterations in the amino acid sequences which do not affect adversely the antigenic nature of the antigen. In particular, antigenic portions of the antigen sequences may be used alone, for example, the regions corresponding to nucleotides 816–863, 1377–1595, 1377–1630 or 1824–1985 of MDV gB, or nucleotides 483–633, 843–933 or 1203–1278 of MDV gC, and minor variations thereof. These sequences and the peptides encoded thereby form further aspects of the invention. In the case of a sequence which is an insertion site, it is necessary only that the sequence should be non-essential for the infectivity and replication of the virus and have sufficient homology with the defined sequence to enable recombination to occur. Thus an insertion of the nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous. It will be appreciated that such degrees of homology relate to substantially the entire portion of each sequence (a) to (f) and (x) defined above. Shorter sequences may be used as probes in the identification or isolation of such longer sequences, but in this case the degree of homology will in general need to be greater in order to ensure accurate hybridization.

Thus, a further aspect of the invention provides subsequences of at least 13 nucleotides having at least 90% (preferably 95%, 99% or 100%) homology to at least one portion of any of the said sequences (a) to (f), (x) and (y) above.

In the above list, sequences (a), (b), and (d) to (f) are useful as antigen-expressing sequences and sequence (y) is useful as an insertion site for heterologous sequences. Sequence (c) is useful for deletion to provide TK– mutants.

The sequences may readily be isolated from naturally-occurring HVT and MDV viruses, using the sequence information given herein and standard techniques, for example involving the preparation of oligonucleotide probes and use thereof to hybridize to the naturally-occurring DNA.

The isolated polypeptides encoded by sequences (a), (b) and (f) above are novel and form a further aspect of the invention, together with minor variations thereof, and any glycosylated forms thereof which result from expression of the said sequences in MDV-susceptible cells.

A second aspect of the invention provides MDV mutants which are insertional or deletional mutants in the TK gene.

The mutation may be in the coding or non-coding sequences of the region identified.

An MDV antigen-expressing gene may be isolated from a virulent strain of MDV and inserted into the TK region of a less virulent strain of MDV; this insertion would result in a novel "virus" if it did not result in a naturally-occurring virus.

Other heterologous antigen-encoding sequences may be included, as well as an MDV antigen-encoding sequence, for example.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursai disease (Gumboro), inclusion body hepatitis (adenovirus), lymphoproliferative disease of turkeys, Newcastle disease, reticuloendotheliosis in chickens, reticuloendotheliosis in turkeys, rotavirus enteritis, turkey haemorrhagic enteritis, and turkey rhinotracheitis. The sequence may alternatively encode paramyosin (a muscle protein common to all invertebrate parasites) or an antiscenic part thereof, somatostatin or a growth-promoting part thereof, or an immune regulator.

The vectors in accordance with the invention will then provide multivalent vaccine protection.

The mutant viruses are potentially useful in vaccines as attenuated viruses, without necessarily having a heterologous sequence inserted.

A convenient process for preparing the deletional or insertional mutants of the second aspect of the invention comprises simply introducing into a suitable cell, for example, by co-transfection, a deletional or insertional mutant version of the TK region and either whole viral DNA or a whole virus (for example, the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells, and duck embryo fibroblasts, all preferably grown in sub-confluent monolayers in Petri dishes. The transfected DNA and the whole viral DNA will then recombine with one another in the infected cells by homologous recombination and the desired recombinants can be screened for, for example, by the detection of hybridization to suitable probes or by an immunoassay using suitable antibodies to the gene product of the region in question.

For homologous recombination to take place, the viral DNA must replicate. At present, no cell-free replication system for MDV is known. However, if such a system becomes available, then the process of the invention could be operated therein. The environment in which the replication and recombination occur is not critical.

Regions (a), (b) and (d) to (f), which were identified above as being responsible for encoding immunologically useful viral antigens, can be inserted into suitable vectors, for example into HVT or other vectors such as fowlpox-virus, bacteria, or fungi. In the case of viral vectors, especially herpesvirus vectors and poxvirus vectors, such insertion can be achieved by recombination between the antigen-encoding sequence, flanked by suitable non-essential sequences, and the vector's genome in a suitable host cell as described above. When HVT is the vector, the promoter will usually be an HVT or MDV vector. When fowlpox-virus or other virus is the vector, the promoter will usually be a promoter which is endogenous to the vector. In the case of bacteria and fungi, the antigen-encoding sequence may be inserted using known or yet-to-be-discovered techniques of DNA manipulation. A non-pathogenic strain of Salmonella may be used as such a host. The heterologous sequence may be inserted into the host's genome or be carried on an independently replicating plasmid. A promoter which is endogenous to the host will usually be used to control expression of the heterologous (viral antigen-encoding) sequence.

The flanking sequences which are used may comprise all, virtually all, or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, three strategies can be envisaged for the construction of improved Marek's disease vaccines: (1) Construction of recombinant HVT that express selected MDV genes; (2) Construction of deletional or insertional mutants of highly virulent strains of MDV, which are attenuated and hence suitable for use in vaccines; (3) Construction of recombinant viruses that express MDV proteins in other vectors such as fowlpox virus.

To prepare a vaccine in which HVT or MDV is the virus or vector, the virus is grown in suitable cells such as chick embryo fibroblasts in a standard culture medium such as 199 medium (Wellcome or Flow Laboratories) for 3 to 4 days at about 37° C. The cells are harvested by trypsinization and suspended in medium containing 10% dimethyl sulphoxide and 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to MDV, including commercially-reared poultry such as chickens, turkeys, ducks, and quail.

BRIEF DESCRIPTION OF THE DRAWINGS

FIGS. 2A–2R (on 18 sheets) show the nucleotide sequence of the gB gene of the RB1B strain of MDV, with the numbering referring to the MDV nucleotides, the sequence of part of the HVT gB gene shown below the line, homologies indicated by vertical bars, and amino acid differences between MDV gB and HVT gB shown above the line.

FIGS. 4A–4H (on 8 sheets) show the nucleotide sequence of most of the HVT gH gene, with the corresponding amino acid sequence shown above the line.

FIGS. 5A–5J (on 10 sheets) show the nucleotide sequence of the HVT TK gene, with the numbering referring to the HVT nucleotides, the sequence of part of the MDV TK gene shown below the line, homologies indicated by vertical bars, and amino acid differences between MDV TK and HVT TK shown above the line.

FIGS. 6A–6F (on 6 sheets) show the nucleotide sequence of the gC gene of the RB1B strain of MDV, with corresponding amino acids shown above the line. The 3' terminal part of this nucleotide sequence encodes an anchoring sequence of the gC glycoprotein encoded by this gene.

FIG. 7 shows part of the nucleotide sequence of the HVT homologue of the VZV62/HSV-1 IE 175 gene, with corresponding amino acids shown above the line.

FIG. 8 shows part of the nucleotide sequence of the HVT ribonucleotide reductase (large subunit) gene with corresponding amino acids shown above the line.

FIGS. 9A–9B (on 2 sheets) show part of the nucleotide sequence of the MDV ribonucleotide reductase (large subunit) gene, with corresponding amino acids shown above the line.

FIG. 10 shows part of the nucleotide sequence of the MDV ribonucleotide reductase (small subunit) gene, with corresponding amino acids shown above the line.

FIG. 11 shows part of the nucleotide sequence of the MDV homologue of the HSV-1 IE-175 gene, with corresponding amino acids shown above the line.

FIG. 12 shows part of the MDV homologue of the HSV-1 IE-68 gene, with corresponding amino acids shown above the line.

Figure 14B-1:
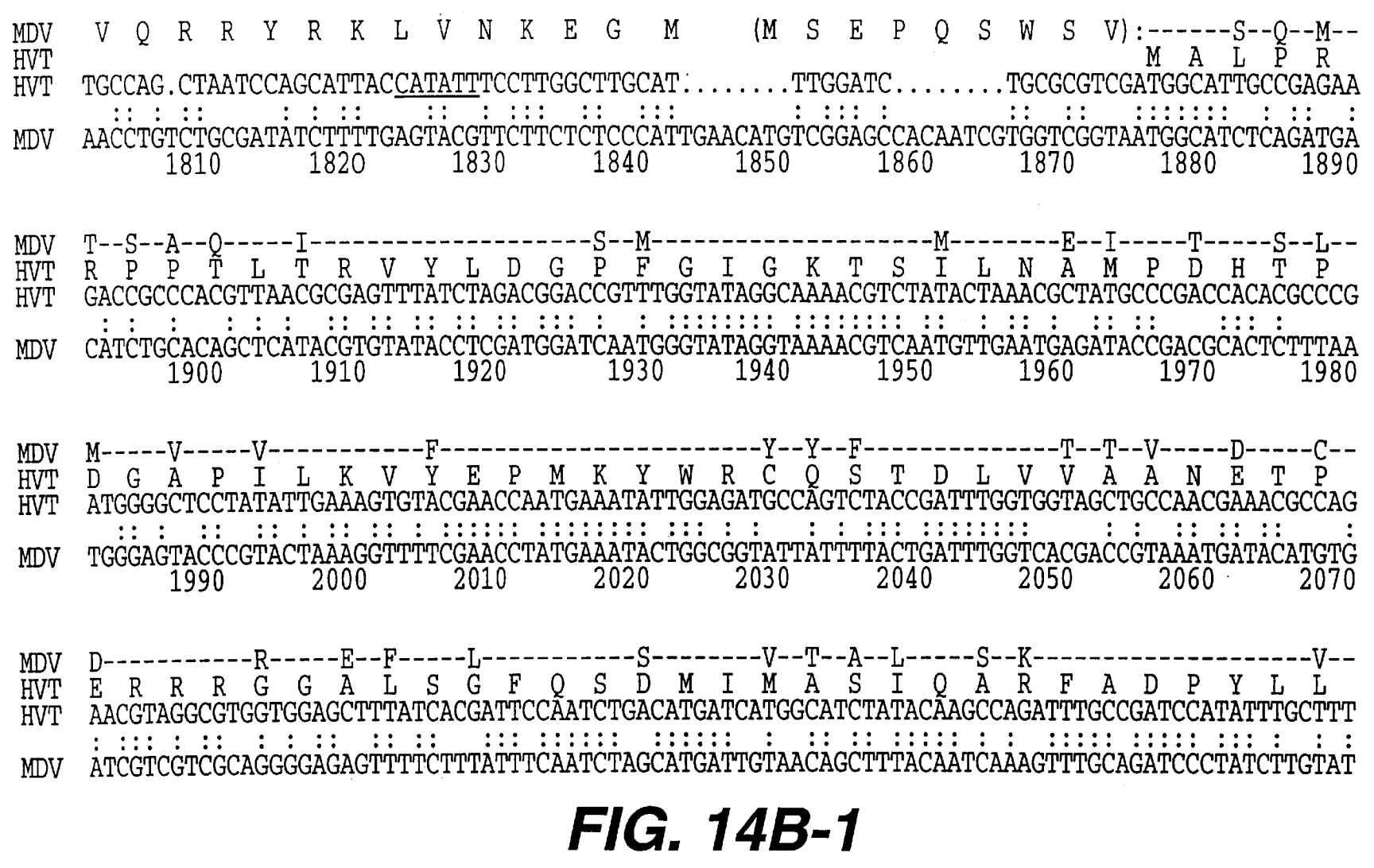
Figure 14C:
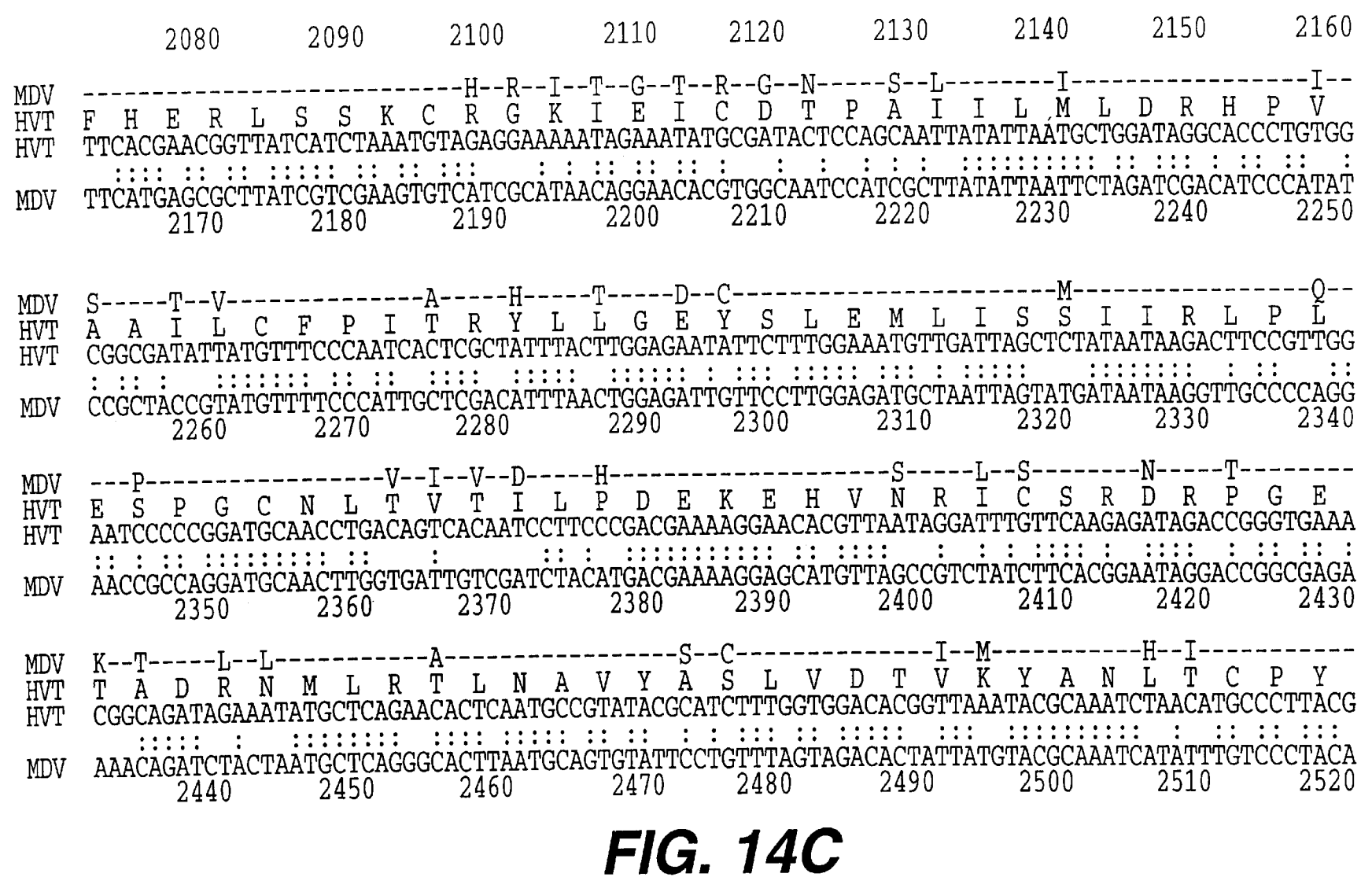
Figure 14C-1:
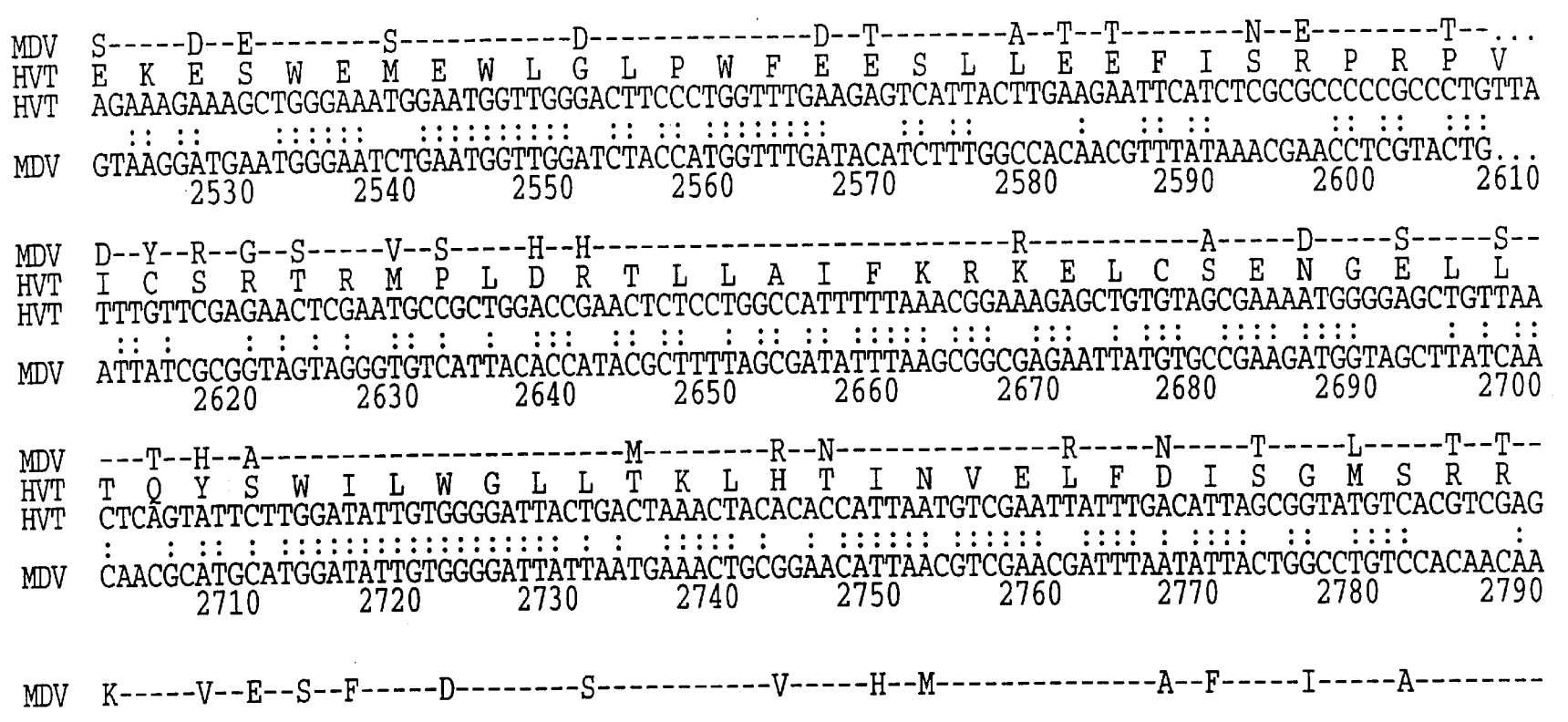
Figure 14D:
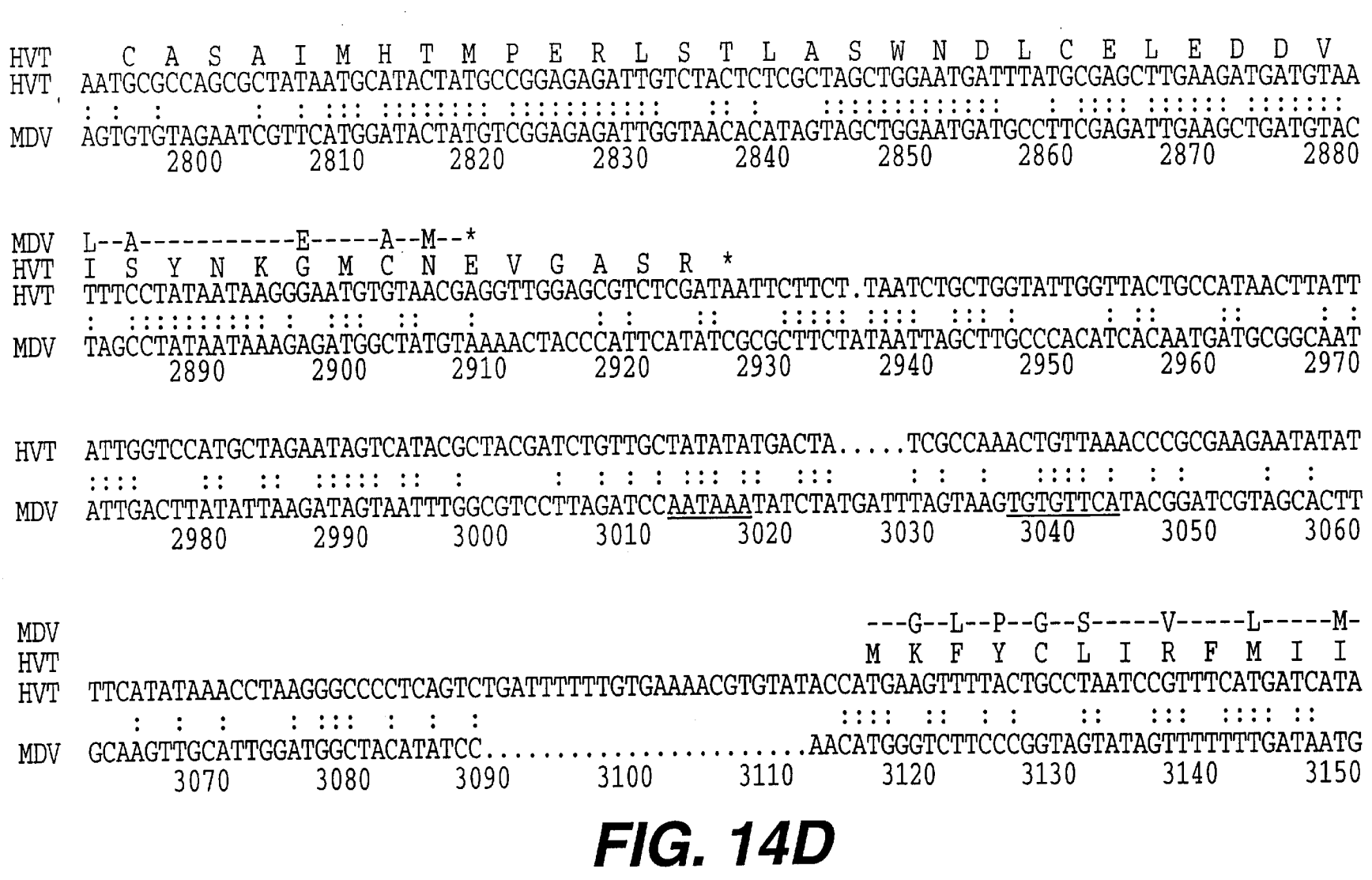
Figure 14D-1:
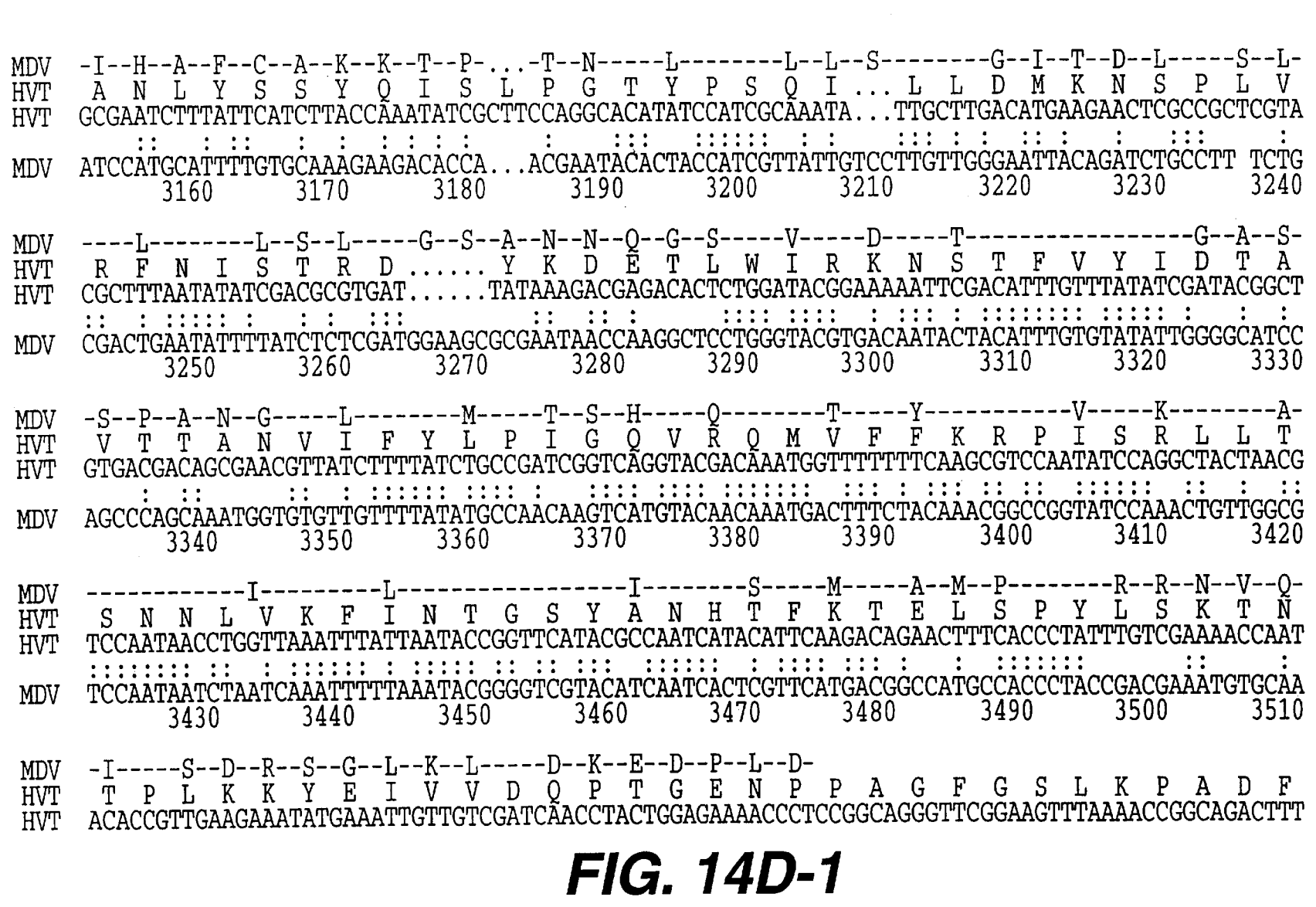

FIGS. 14A–14F (on 11 sheets) supplement FIGS. 4 and 5, and show the nucleotide and predicted amino acid sequences from the region containing the MDV and HVT TK and gH and flanking genes. The bracketed MDV amino acid sequences are those potentially encoded by this region of nucleotide sequence if the upstream ATG triplet were the true gene initiation site. Asterisks denote stop codons. Spaces have been inserted into the sequences in order to optimize alignments. Colons between the MDV and HVT DNA sequences indicate nucleotides conserved between the two viruses. MDV amino acids are only shown in positions where they differ from that in HVT.

FIG. 15 shows the partial nucleotide sequence of the MDV homologue of HSV gD, the predicted amino acids being shown above the MDV nucleotide sequence.

DESCRIPTION OF THE PREFERRED EMBODIMENTS

Figure 1:
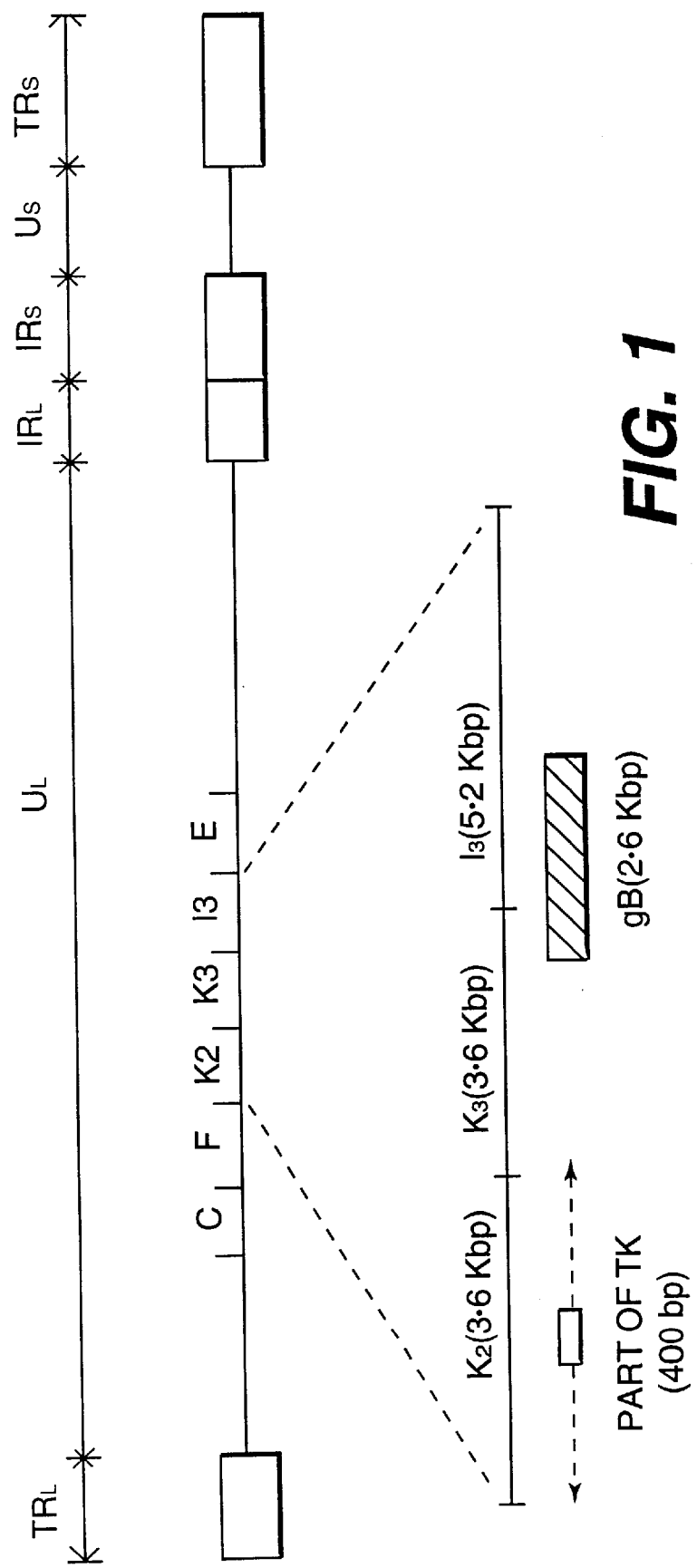
FIG. 1 is a map of the MDV genome showing in part the BamHI site distribution and the location of the gB and TK genes.

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains. The 'highly oncogenic' strain RB1B of MDV [Schat, K. A. et al (1982) Avian Pathol. II, 593–605] was obtained from Professor B. Calnek, Cornell University, Ithaca, N.Y., U.S.A. The virus received has been plaque purified in chicken kidney cells in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525–538], obtained from the Wellcome Research Laboratories, Beckenham, Kent, had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

Tissue culture. CEF were grown in roller bottles in 199 medium (Wellcome), supplemented with penicillin, streptomycin, Fungizone®, and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530].

Isolation of IDV DNA. Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer PH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 and ImM EDTA (TE).

Cloning of MDV DNA. One $\mu$g of MDV DNA was cut with the restriction enzyme BamHl and ligated to BamHl-cut, dephosphorylated pUC13 DNA (Pharmacia). Competent E-coli strain TGI cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 72, 3961]. Positive colonies were cultured in small volume and plasmid DNA isolated by the procedure of Holmes, D. S. and Quigley, M. [(1981) Anal. Biochem. 114, 193–297]. The size of the inserts was determined by electrophoresis of BamHl digests of the recombinant DNA in agarose gels. Plasmids containing MDV inserts ranging from less than 1 to 18 Kbp were obtained.

Random sequencing of viral DNA. Sonicated fragments of viral DNA were cloned into SmaI-cut, dephosphorylated M13.mpl0 (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{35}$S dATP.

The same procedure was used to sequence cloned fragments of MDV DNA except that plaques were identified by hybridization to labelled insert so as to avoid colonies containing pUC13 fragments.

The present invention will be better understood by reference to the following examples, which are merely illustrative of the invention and are not intended to limit the scope of the invention, which is defined in the claims appended hereto.

EXAMPLE 1 gB Gene of MDV

An M13 clone of HVT homologous to the gB gene of VZV and HSV hybridized to BamHl fragment I3 of MDV (see FIG. 1). Sequencing of this fragment obtained from a BamHl library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses, such as the alignment of cysteine residues and the presence of hydrophobic sequences which are presumably capable of spanning a lipid bilayer [Pellet, P. E. et al (1985), J. Virol. 53, 243–253]. However, MDV gB has only 48% amino acid similarity with gB of HSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

EXAMPLE 2 gH Gene of HVT and gH Gene of MDV

Figure 3:
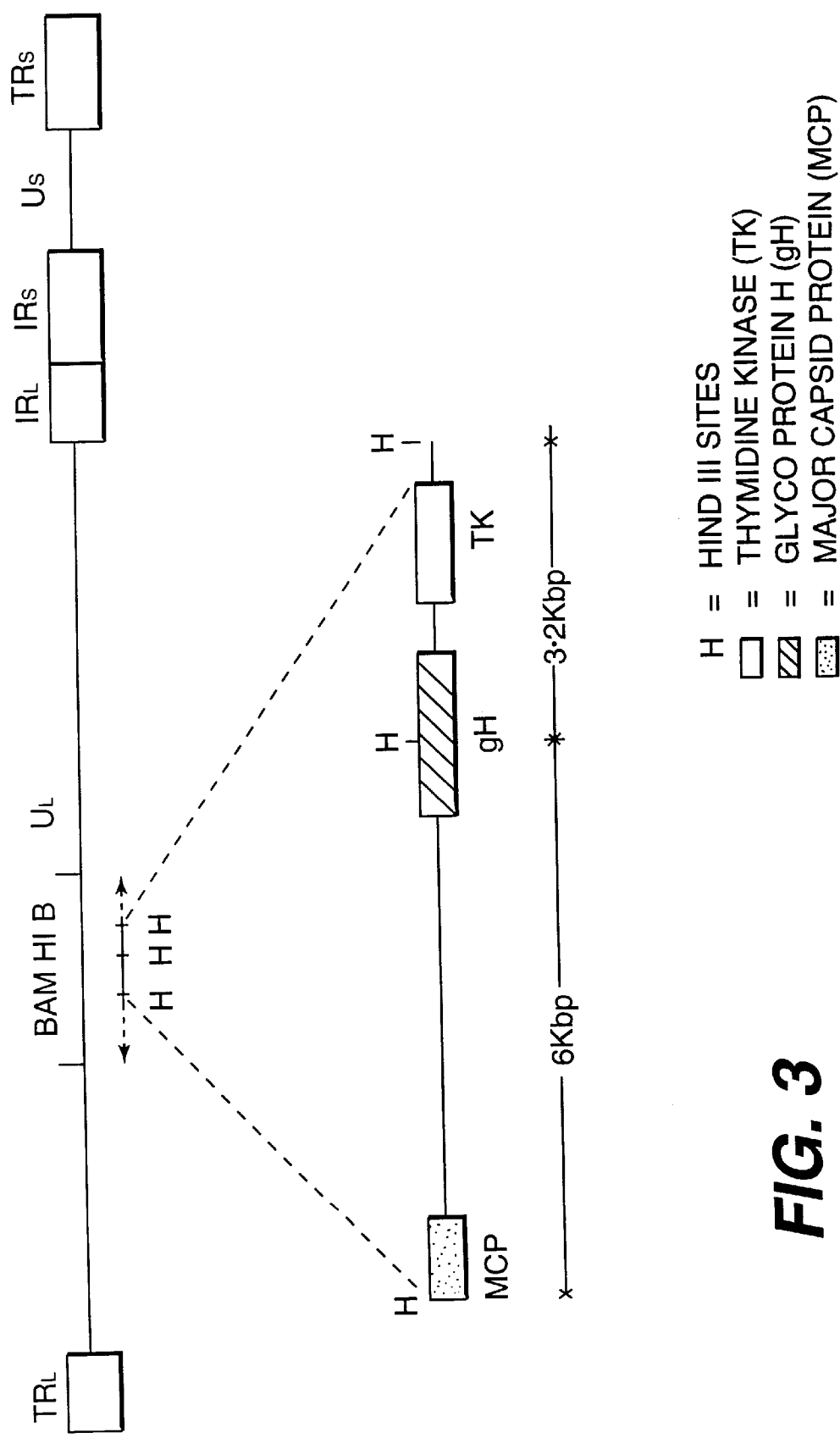
FIG. 3 is a map of the HVT genome showing the positions of the gH (hatched), TK (solid black), and major capsid protein (MCP, dotted) genes, with HindIII sites shown as "H".
Figure 13:
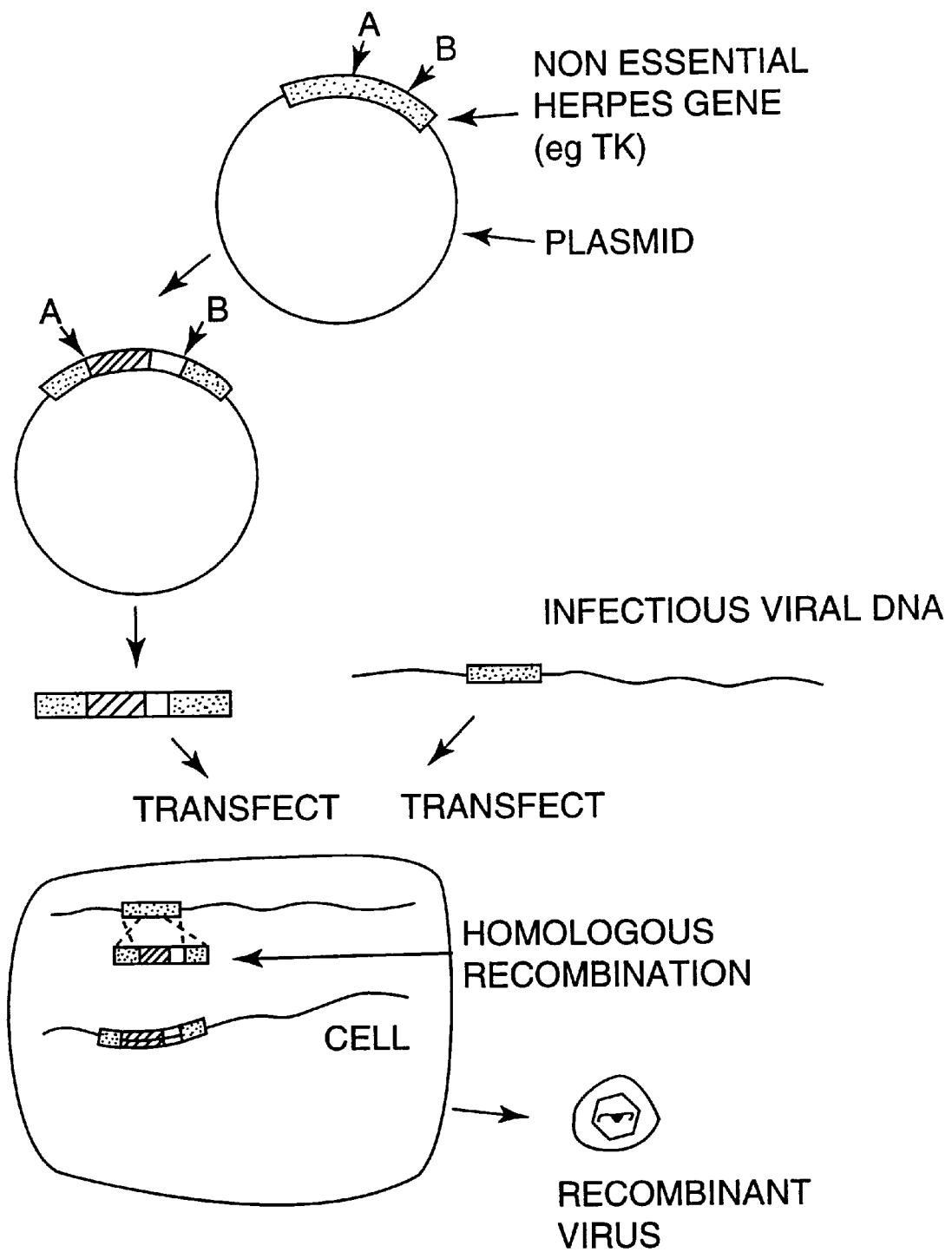
FIG. 13 is a schematic representation of homologous recombination at a non-essential region of a viral genome and a homologous region of DNA cloned within a plasmid vector.

An M13 clone of HVT containing sequences homologous to HSV gH was isolated during our earlier work on gene identification and mapping [Buckmaster et al (1988) as above]. This clone, when used as a probe, hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24, and 20, respectively (estimated from maximised amino acid overlaps of 630, 644, and 153, respectively).

EXAMPLE 3

TK Gene of HVT and TK Gene of MDV

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamHl K2 fragment of MDV (FIG. 1). The complete sequence of MDV TK gene is shown in FIG. 14. Comparison of the MDV and HVT TK sequences shows that the two genes have 60% amino acid identity. By contrast, the % amino acid identities between the TK gene of HVT and the TX genes of HSV 1, VZV, and EBV are only 30, 27, and 24, respectively (estimated from amino acid overlaps of 320, 332, and 193, respectively). The predicted amino acid sequences of HVT and MDV TK show characteristic ATP and/or CTP binding site motifs described for a number of virus and eukaryotic proteins that are associated with phosphorylation [Gentry, G. A. (1985) Proc. Natl. Acad. Sci. U.S.A. 82, 6815–6819]. These conserved sequences are examples of useful sites for insertion and expression of foreign genes and for producing TK– deletion mutants.

EXAMPLE 4

A antigen Gene of MDV (gP57–65) (gC Homologue)

The A antigen gene is of interest in vaccine development, both as an immunogen (it encodes a major glycopolypeptide product) and also because we have identified it as the homologue of HSV gC, a potential non-essential region. The A antigen gene was mapped within the BamHI B fragment of MDV (Isfort et al 1987). The MDV GA strain was used. A 2.2 kbp Pvu II-Eco RI fragment was obtained and identified as containing the sequence encoding the A antigen. The nucleotide sequence was determined for the GA strain of MDV [Coussens and Velicer, Abstract OP18.51, VII International Congress of Virology, 9–14 August, (1987) Edmonton, Canada; J. Virol. 62, 2373–2379]. The sequencing work of Coussens et al was made on the same fragment as that identified by Isfort et al. During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoRl cleaved pUC13 vector by standard protocols. One plasmid (pMB419) was sequenced by the M13 dideoxynucleotide method. The sequence of the MDV RB1B A antigen and the predicted amino acid sequence of the protein are presented in FIG. 6. The gC gene shown in FIG. 6 is of a very virulent strain of MDV which can be distinguished from the standard MDV isolates such as the MDV GA used by Isfort et al and Coussens et al in that it can cause disease in chickens which are normally genetically resistant to Marek's disease or which have been vaccinated with HVT. Furthermore, a direct comparison between the predicted amino acid sequence of the A antigen encoded by the RBIB strain of MDV and that of the A antigen encoded by the GA strain of MDV showed extensive sequence divergence in the carboxy-terminal region, as well as a variation at the amino terminal of the protein close to the predicted cleavage site of the signal sequence [Binns et al (1989) Virus Research 12, 371–382]. Moreover, as pointed out above, the 3' terminal part of the nucleotide sequence shown in FIG. 6 encodes an anchoring sequence of the gC glycoprotein. Although Coussens et al sequenced the structure of the gC gene, the sequence of the present invention is new, because it is very different from the Coussens et al sequence with respect to the 3' terminal portion. In particular, nucleotides 1408–1500 of Coussens et al differ from nucleotides 1708–1800 of the gC gene of the present invention.

The C-terminal portion of the glycoprotein encoded by the Coussens et al gene differs from the C-terminal portion of the glycoprotein encoded by the gC gene of the present invention. The difference is very important since that region of the gene is crucial for the localization of the glycoprotein gC in the cell after synthesis. The gC encoded by the Coussens et al gene does not contain any anchor sequence with the result that the gC of Coussens et al is secreted into the extracellular medium.

The question of localization was raised by Coussens et al at page 2378, right hand column, second paragraph, wherein it was stated that a carboxyl-terminal membrane anchor sequence is possible. However, the MDV gp57–65 obtained by Coussens et al presented a predominantly secretory nature. Coussens et al therefore concluded that it was not clear whether the small amount of mature gp57–65 is actually anchored in the plasma membrane or held by other interactions.

That point made by Coussens is very important since the presence or absence of anchor sequences makes the glycoprotein totally different in terms of antigen presentation to the cells of the immune system. The gC of the present invention includes the anchor sequence. Thus, gC remains fixed to the membrane, resulting in the presentation of the gC of the present invention.

Figure 16:
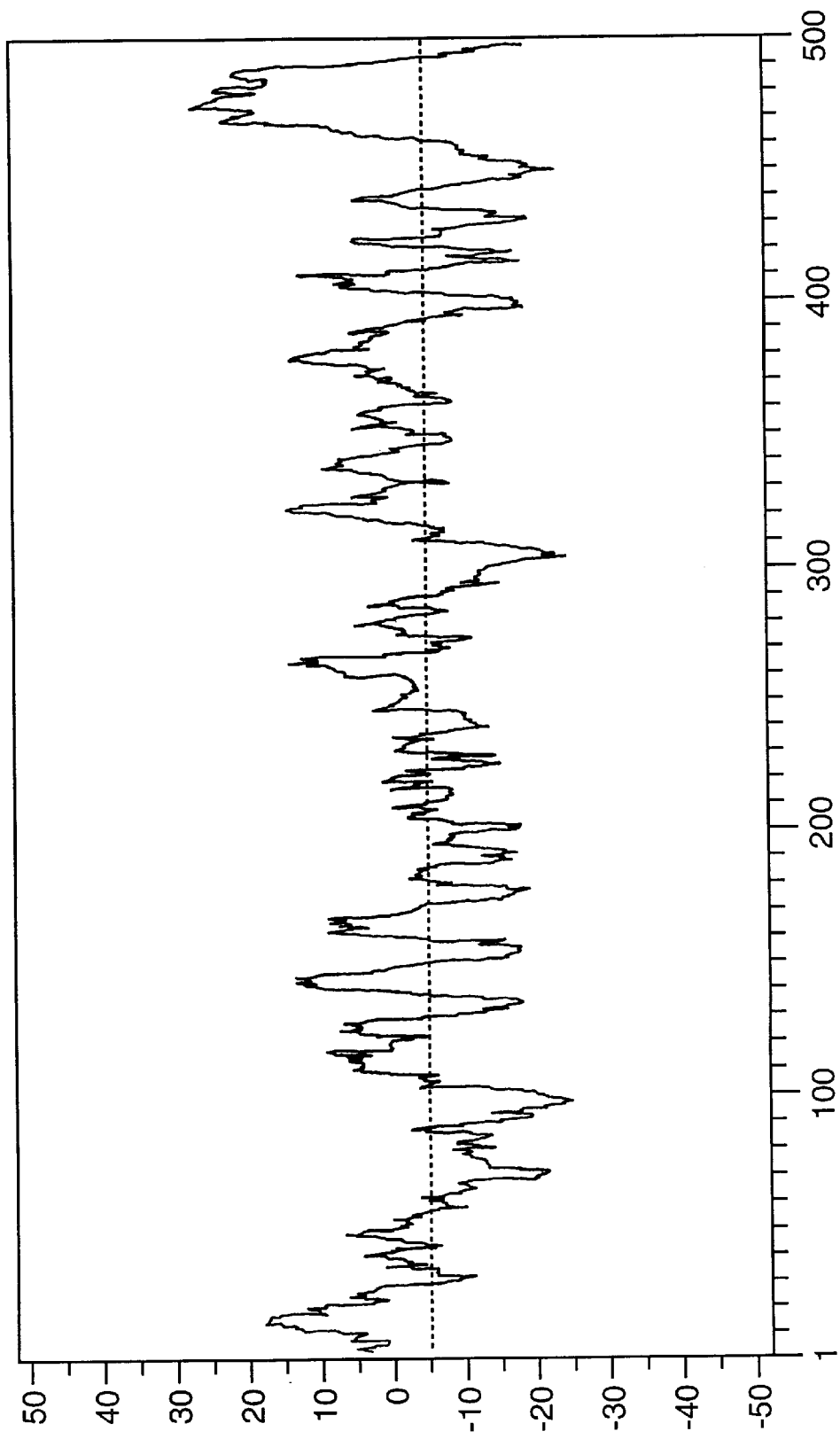
FIG. 16 is a hydropathic index plot of the glycoprotein encoded by the RBIB gC gene.
Figure 17:
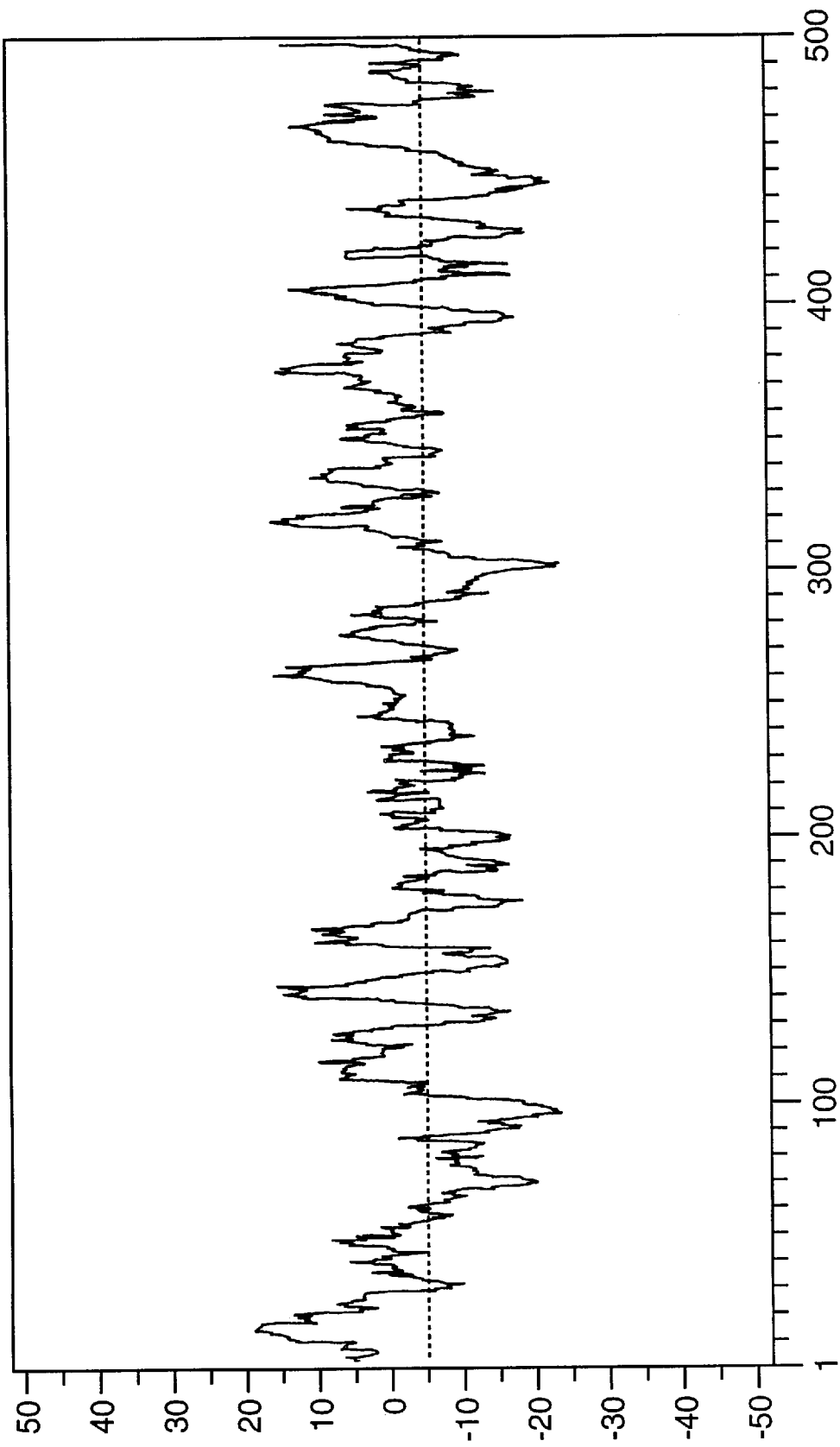
FIG. 17 is a hydropathic index plot of the glycoprotein encoded by the MDV GA A antigen gene.

The absence of an anchor sequence in the gC of Coussens et al has been determined by a study of the hydropathic index from amino acid 1 to amino acid 505 by means of the computer program named SOAP (Intellegenetics PC gene packaged software, Palo Alto, Calif. Also see G. Kyte et al., a drill molecular biology, 1982, 157: 105–132; and P. Kline et al., biochimica biophysica acta 1985, 815: 468–476.) The results of this SOAP study are shown in FIGS. 16 and 17.

As can be seen from a comparison of the hydropathic indices of the gC of Coussens et al (FIG. 17) with the gC of the present invention (FIG. 16), the sequence gC at amino acids 460–500, according to the present invention, is different from the Coussens et al gC sequence, and this difference is crucial as manifested by differences in secretion mode and immunogenicity of the glycoproteins.

The A antigen regions of MDV and HVT are non-essential genes and they can therefore be used as sites in MDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.

2) On conducting a similarity search it became clear that the MDV A antigen gene is the homologue of HSV gC and PRV gpIII glycoproteins. Both of these homologous genes are known to be non-essential [for the HSV homologue, see Rosenthal et al (1987) J. Virol. 61, 2438–2447].

3) Strains of MDV lacking A antigen as judged by agar gel diffusion tests [Churchill, A. E. et al (1969) J. gen. Virol. 4, 557–564] or producing low levels using the more sensitive 2D radio-immunoprecipitation [van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

Strategies for Introducing Genes into HVT Vectors

Two possibilities can be envisaged: 1) insertion into non-essential genes of the vector, or 2) substitution of foreign gene for corresponding gene of the vector. This would be possible only in regions which already have substantial homology as may be the case between some genes of MDV and HVT.

EXAMPLE 5

Insertion into Non-essential Genes of HVT or MDV (a) Insertion at the TX locus of the vector.

1) HVT or MDV may be used as vectors for insertion and expression of avian herpesvirus genes. In particular gB, gH or gC of RB1B MDV may be inserted into HVT. One may use the promoter associated with the inserted gene or use heterologous promoters, including those of a different class of genes (for example, the immediate early promoter to optimize expression of gB).

2) HVT or MDV may be used as general vectors for the insertion and expression of genes unrelated to avian herpes viruses and likely to require manipulation of promoters for optimal expression. The procedure to be used for gene insertion is substantially as described previously for the insertion of hepatitis antigen in HSV [Shih et al, 1984 as above].

MDV and HVT DNA, obtained as described above, is infectious provided that precautions are taken not to shear the DNA during extraction. Calcium phosphate precipitates of viral DNA prepared as described by Stow and Wilkie [(1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinized, replated (1:1 or 1:2) in 199 medium (Wellcome) containing 2 to 4% calf serum, and incubated at 37° C. until plaques developed, usually after 4 to 5 days. Approximately 200 plaques may be obtained per μg of HVT DNA and approximately 50 per μg of MDV DNA.

For homologous recombination and isolation of recombinant virus, genes of interest are inserted within non-essential genes such as TK or gC and co-transfected with wild-type viral DNA at molar ratios ranging from 10:1 to 2:1, as described above. Alternatively, intact wild-type virus may be used for co-infection.

Restriction enzyme sites that could be used for the insertion of foreign antigens into the TK of HVT strain Fc-126 include: BanII, Bsp1286, DraIII, EcoRl, HincII, HpaI, NheI and, NspbII.

RE sites that could be used to produce defined TK deletion mutants in MDV serotype I strain RE13 include; BalI, HaeII, NdeI and SphI as insertion sites for foreign DNA that would disrupt the TK gene, and double digests of combinations of these four restriction enzymes (EcoK could also be used) to remove a portion of the TK gene, thus inactivating it.

Some of these enzymes also have sites in the plasmid vector into which the virus DNA fragments are cloned. Thus, in order to linearize the clone DNA without also cutting within the vector, partial digests may be carried out.

None of the above enzymes should cause any disruption to flanking genes, HSV-1 homologues of which are known to play an important role in virus multiplication.

Virus recombination may be detected by 'plaque lifts', which involve transfer of infected cells and released virus which have adhered to the agar overlay to nitrocellulose and hybridization of the denatured DNA released from the cells and virus to suitable probes as described by Villareal, L. et al [(1977) Science 196, 183–185]. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system, such as labelled protein A or phosphatase-conjugated antiglobulin antibody.

The gene of interest with appropriate promoters is first inserted within the cloned TK gene. The recombinant DNA is then co-transfected with infectious DNA of the vector in chick embryo fibroblasts or chicken kidney cells and TK− virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus, the use of an immediate early promoter may allow expression in latently infected cells.

(b) Insertion at other non-essential sites of the vector. Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or with specific antibody allows the isolation of recombinants.

An antigen-encoding sequence can also be inserted into the ribonucleotide reductase (large subunit) gene of HVT or of MDV—see FIGS. 8 and 9.

EXAMPLE 6

Substitution of MDV Genes for Their Homologues in HVT

Substitution may be achieved by co-transfection of cloned MDV sequences and infectious HVT DNA as described in Example 5. Substitution of the gB and gC genes derived from the RB1B strain of MDV for their counterparts in HVT may be effected as may substitution of the gH gene of MDV, other glycoproteins, and immediate early genes.

Recombinants expressing MDV sequences and epitopes may be detected using MDV-specific monoclonal antibodies or anti-peptide anti-bodies raised against unique MDV sequences as described above.

The advantage of this procedure is that it is relatively simple and does not require manipulation of promoters. However, it may be limited to genes which share substantial homology.

EXAMPLE 7

Strategies for Obtaining TK− Mutants of MDV Deletion Mutants

Deletions may be introduced within any suitable part of the gene, for example, the domains of the gene that are required for nucleoside binding. This may be achieved by restriction enzyme double digestion, for example, with HaeII and any of the following enzymes: BalI, NdeI, SphI or EcoK. Appropriate fragments are then relegated, followed by co-transfection with infectious viral DNA or transfection into virally-infected cells. Reference may be made to FIGS. 7 and 8, and to the section above relating to insertion of heterologous sequences, in choosing restriction enzymes and so on. TK− virus may be selected in the presence of acyclovir [Ross, N. (1985) as above] or FMAU [Schat, K. A. et al (1984) as above]. Plaque-purified clones may then be tested for the absence of the deleted portion of the TK gene by hybridization.

The deletion mutants of MDV may be used themselves as attenuated viruses for vaccine preparation, or may have sequences for heterologous antigens inserted.

Insertional Mutants

A functional β-galactosidase gene under the control of a herpesvirus promoter, or any other suitable sequence, or a single base is first introduced in a domain of the TK gene which is essential for TK activity. The recombinant DNA is then co-transfected with infectious viral DNA or transfected into virally-infected cells to allow homologous recombination to occur. Selection in the presence of acylovir or FMAU will yield TK− insertional mutants. If a β-galactosidase gene is introduced, mutants can be detected by the production of blue plaques in the presence of X-gal.

The TK gene and surrounding sequences may be subcloned into another suitable vector, if necessary.

EXAMPLE 8

Insertion of MDV RB1B gB Gene into HVT

The HVT TK gene is cloned in the plasmid vector pUC13 to generate a plasmid, which is termed pTX1B. This plasmid is linearised with, for example, the restriction endonuclease RsrII which cleaves the plasmid only within the TK gene (nucleotide position 197 in FIG. 5, enzyme recognition sequence CGGACCG). The "sticky" ends thus generated can be end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which may be termed RB1B-BamHI-I$_3$ and RB1B-BamHI-K$_3$. (Note I$_3$ had lost one BamHI site during cloning.) To generate a complete gB copy on one plasmid, both plasmids were cleaved with BamHI and the fragments ligated. Recombinants containing the desired configuration were identified by restriction enzyme analysis of plasmid DNA'S. However, as described above, the complete gB sequence was subsequently obtained on an EcoRI/SalI fragment.

Further information regarding the sequence encoding MDV gB and its manipulation may be found in Ross et al [J. gen. Virol (1989) 70 1789–1804].

The single recombinant plasmid of Ross et al is then cleaved with EcoRI and SalI, the ends are repaired, and the plasmid is cloned into PTK1B prepared as above. Alternatively, the MDV gB open reading frame could be excised from plasmid MSB27 by digestion with HincII and NaeI and the products ligated to HVT TK plasmid pTK1B, cleaved partially with HpaI. Recombinant plasmids containing both TK and gB sequences could be identified by hyrbridization and further characterized by Southern blotting. The recombinant plasmids are then introduced into cells containing HVT virus (viral DNA) and homologous recombination will introduce the gB gene into the TK gene. HVT viral recombinants can be selected with acyclovir or FMAU or alternatively detected with labelled gB probes.

EXAMPLE 9

RB1B gC (A Antigen) Gene into HVT

Blunt ended PTK13 is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTX1B as in Example 8. (The cloning can be verified by analysis of the resulting clones with restriction enzymes, probing with radioactively labelled fragments, or DNA sequencing, or any combination of these).

The resulting plasmid with the RB1B gC gene cloned into the HVT TK gene can then be introduced into the HVT genome by transfecting the plasmid into HVT-infected cells using calcium phosphate precipitation or electroporation. Homologous recombination, involving cross-overs either side of the gC gene, between the HVT virus and the flanking sequences of the HVT TK plasmid will carry the RB1B gC gene into the HVT viral genome. Viral recombinants can be selected for (as they are TK−) or identified (e.g. by probing) as described above.

In analogous ways, the sequence information given above and in the Figures can be used to design cloning strategies for the insertion of these genes and others into the non-essential genes of the HVT described here or to generate combinations of antigen genes in HVT.

EXAMPLE 10

MDV gD Gene

FIG. 15 shows part of the sequence of the MDV gD gene. The sequence was obtained by sequencing random fragments of the $U_s$ region MDV DNA and comparing the sequence to the sequence of known herpesvirus genes (see Buckmaster et al, loc. cit.). The sequence gave homology scores of 189 and 216, respectively, with HSV gD and PRV gp50. The sequence information assists in the preparation of suitable probes to isolate and characterize the gene.

What is claimed is:

1. A vaccine against Marek's Disease, comprising a vector which contains a DNA fragment encoding the gH gene from MDV serotype 1 or 2 or 3.

2. A vaccine according to claim 1, wherein the vector is a viral vector and the said DNA fragment is inserted into a non-essential site of said viral vector.

3. A vaccine according to claim 1 or 2, wherein the DNA fragment comprises the coding portion of the nucleotide sequence appearing on FIG. 14 from nucleotide 3115.

4. A vaccine according to claim 1, wherein the DNA fragment comprises the coding portion and at least a part of the 5' or 3' non-coding portions of the gH gene.

5. A vaccine according to claim 1 or 2, wherein the vector comprises further a promoter which is heterologous to the said DNA fragment.

6. A vaccine according to claim 1, wherein the viral vector is MDV.

7. A vaccine according to claim 6, wherein the MDV vector is HVT.

8. A vaccine according to claim 5, which comprises MDV-susceptible cells and said viral vector.

9. A vaccine according to claim 2, wherein the vector is a Poxvirus.

10. A vaccine according to claim 9, wherein the Poxvirus is a fowl poxvirus.

11. DNA fragment comprising the nucleotide sequence of FIG. 14 from nucleotide 3115.

12. A vector comprising a DNA fragment according to claim 11, which is suitable for transfection of an MDV-or-HVT-susceptible cell.

* * * * *